United States Patent [19]
Shaskan

[11] Patent Number: 5,916,906
[45] Date of Patent: Jun. 29, 1999

[54] COMPOSITIONS COMPRISING NICOTINYLALANINE AND AN INHIBITOR OF GLYCINE CONJUGATION OR VITAMIN B6

[76] Inventor: Edward G. Shaskan, 278 Tunxis Rd., West Hartford, Conn. 06107

[21] Appl. No.: 08/930,234

[22] PCT Filed: Mar. 13, 1996

[86] PCT No.: PCT/US96/03435

§ 371 Date: Sep. 12, 1997

§ 102(e) Date: Sep. 12, 1997

[87] PCT Pub. No.: WO96/28167

PCT Pub. Date: Sep. 19, 1996

Related U.S. Application Data

[63] Continuation-in-part of application No. 08/581,394, Dec. 29, 1995, abandoned, which is a continuation-in-part of application No. 08/403,676, Mar. 14, 1995, abandoned.

[51] Int. Cl.⁶ .......................... C07D 213/79; A01N 43/40; A61K 31/60
[52] U.S. Cl. ........................... 514/356; 514/351; 514/353
[58] Field of Search ..................................... 514/351, 353, 514/356

[56] References Cited

PUBLICATIONS

Chemical Abstracts AN 1977:118750, Yeh et al., Jan. 1977.

*Primary Examiner*—Keith D. MacMillan
*Attorney, Agent, or Firm*—Morgan & Finnegan, LLP

[57] ABSTRACT

This invention relates to compositions comprising nicotinylalanine (NAL) and/or related analogues, and an inhibitor of glycine conjugation, either synthetic or naturally occurring. Vitamin B6 may also be present in the compositions of this invention in place of, or in addition to, the inhibitor of glycine conjugation. The compositions may be pharmaceutical in nature. The compositions are useful for inhibiting cellular poly(ADP-ribose) polymerase (PARP, PARS, poly (ADP-ribose) synthetase), an enzyme which causes cellular toxicity and which is activated in a variety of toxic and pathological conditions. PARP is inhibited by some metabolites of the tryptophan oxidative pathway, including nicotinamide, kynurenic acid and xanthurenic acid, which are induced by interferon-gamma. The NAL-containing compositions of the invention enhance the intracellular levels of these metabolites, and thereby augment the natural defense of interferon-induced inhibition of PARP. PARP is implicated in various pathological conditions, including neurodegenerative disorders, viral infections such as AIDS, autoimmune diseases and cancer. Accordingly, this invention also relates to methods of reducing cellular toxicity, and treating or preventing such diseases, by increasing cellular concentrations of nicotinamide, kynurenic acid and xanthurenic acid using the compositions of this invention.

67 Claims, 8 Drawing Sheets

COMPOSITIONS COMPRISING NICOTINYLALANINE AND AN INHIBITOR OF GLYCINE CONJUGATION OR VITAMIN B6

REFERENCE TO RELATED APPLICATIONS

This is a continuation-in-part application of U.S. patent application Ser. No. 08/581,394 filed Dec. 29, 1995, now abandoned, which is a continuation-in-part application of pending U.S. patent application Ser. No. 08/403,676 filed Mar. 14, 1995, abandoned, which are both incorporated herein by reference.

FIELD OF THE INVENTION

This invention relates to methods and compositions useful for reducing cellular toxicity, in vitro and/or in vivo, associated with increases of poly-(ADP)-ribosylation reactions. This invention also relates to pharmaceutical compositions useful for treating diseases for which increasing endogenous concentrations of nicotinamide provide a therapeutic benefit, and methods of treating disease using these compositions. Specifically, this invention relates to compositions comprising nicotinylalanine, and/or related analogues, and an inhibitor, such as aspirin, of glycine conjugation, a metabolic process leading to the metabolism of nicotinamide and optionally B6. In other useful compositions of this invention B6 may be substituted for the glycine conjugate inhibitor. The diseases for which the compositions and methods of this invention provide a therapeutic benefit involve poly (ADP)-ribosylation reactions which contribute to pathogenesis. Such diseases include neurodegenerative diseases, infectious diseases, cancer and certain forms of diabetes.

BACKGROUND OF THE INVENTION

Cellular toxicity associated with poly (ADP)-ribosylation reactions resulting from DNA damage contributes to pathogenesis of several types of diseases. Poly (ADP)-ribosylation reactions have been shown to be associated with the cellular damage occurring in neurodegenerative diseases, autoimmune diseases, infections and cancer.

Several mechanisms, including increases in nitric oxide may contribute to activation of poly (ADP-ribose) synthetase which catalyzes the poly (ADP)-ribosylation reaction. Cleaver J. E. & Morgan W. F., *Mutat. Res.* 257:1–18, 1991; Snyder S. H., *Science, U.S.A.,* 265: 723, 1994; Zhang J. & Snyder S. H., *Proc. Natl. Acad. Sci., U.S.A.,* 89:9382–9385, 1992; DeMurcia G., et al., *Bio Essays,* 13:455–462, 1991. Nitric oxide is produced in a variety of cell types including neurons and blood endothelial cells. Kandel E. R., Schwartz J. H, Jessell T. M., *Principles of Neural Science. Third Edition,* 1991, p191. Nitric oxide is also significant as a possible pathogenic agent for multiple populations of cells because, besides being toxic to the cells in which nitric oxide is produced, nitric oxide is also released into blood where it acts as a "local hormone". Id. In addition, nitric oxide is capable of readily passing across cell membranes into adjacent cells. Id.

Activation of poly (ADP-ribose) synthetase is reported to be associated with the pathogenesis of a variety of neurodegenerative disorders in response to the generation of toxic quantities of nitric oxide. Zhang J. et al., *Science. U.S.A.,* 263:687–689, 1994. Generation of nitric oxide in neurons occurs in response to over-stimulation of NMDA receptors by naturally occurring excitotoxic agents present in the brain including, for example, glutamic and quinolinic acids. Inhibitors of nitric oxide production provide protection against the pathogenic effects of the excitatory agents. Dawson V. L., et al., *Proc. Natl. Acad. Sci., U.S.A.,* 88:6368–6371, 1991.

Inhibition of poly (ADP-ribose) synthetase activity has also been associated with the action of anti-viral agents inhibiting gene expression in HIV-1, the virus causing AIDS. Yamagoe S., et al., *Molec. Cell. Biol.,* 11:3522–3527, 1991. For example, both nicotinamide and benzamide, known inhibitors of poly (ADP-ribose) synthetase, when added to cultures of HIV-1 infected cells demonstrated significant antiviral activity. Id. Further support for such a mechanism mediating antiviral activity of nicotinamide comes from recent studies linking cellular HIV-1 infection with decreased levels of nicotinamide adenine dinucleotide (NAD) and a significant antiviral effect of nicotinamide treatment of HIV-infected cells in culture (Murray MF et al., *Biochem. Biophys. Res. Commun.,* 210:954–959, 1995; and, Murray MF et al., *Biochem. Biophys. Res. Commun.,* 212:126–131, 1995). In addition, relevant to HIV-1 associated encephalopathy, it has been reported that the HIV-1 coat protein, gP120, kills neurons in cell culture by a mechanism involving nitric oxide. Dawson V. L., et al., *Proc. Natl. Acad. Sci.. U.S.A.,* 90:3256–3259, 1993. Like neuronal cells, toxicity of nitric oxide in HIV-1 infected cells, and other cells infected by virus of several types (Goldman N., et al., *Cell* 24:567–572, 1981; Déry C. V., et al., *Virus Res.* 4:313–329, 1986; Mansuri M. M. & Martin J. C., *Ann. Rep. Med. Chem.* 24:133–140, 1991) is at least partially caused by activating poly (ADP-ribose) synthetase.

Enhancement of poly-(ADP)-ribosylation has also been reported to be associated with the pathogenesis of certain forms of diabetes. Destruction of the beta cells of the pancreas, which cells make and release insulin, is also associated with nitric oxide toxicity resulting in overactivation of poly (ADP-ribose) synthetase. Kallman, B., et al., *Life Sci.* 51:671–678, 1992; Suarez-Pinzon W. L., et al., *Endocrinology* 134: 1006–1010, 1994.

Involvement of poly (ADP-ribose) synthetase in the development of certain cancers has also been reported. Borek C., et al., *Proc. Natl. Acad. Sci.. U.S.A.,* 81:243–247, 1984; Tseng A. Jr., et al., *Proc. Natl. Acad. Sci. U.S.A.,* 84:1107–1111, 1987; and Alderson T., *Biolog. Revs.* 65:623–641, 1990.

Despite the various reports establishing a pathogenic action of poly (ADP-ribose) synthetase induction, there are few, if any treatments which are suitable for administration to an individual and which result in therapeutic decreases in poly (ADP-ribose) synthetase. In preparations of crude or partially purified enzyme, nicotinamide and a number of benzamide derivatives are effective inhibitors of poly (ADP-ribose) synthetase. Banasik M., et al., *J. Biol. Chem.,* 267:1569–1575, 1992. Despite their effectiveness at inhibiting poly (ADP-ribose) synthetase, nicotinamide and benzamide have only limited applicability for therapeutic applications because of their polar nature. Accordingly, millimolar concentrations of these compounds are required to achieve sufficient intracellular uptake and localization to appropriate intracellular target organelles such as the nucleus.

Nicotinamide is an intermediate in the metabolism of the amino acid tryptophan to nicotinamide adenine dinucleotide (NAD) and to nicotinuric acid. Tryptophan is metabolized by the kynurenine pathway, illustrated below, which branches to produce the excitotoxin quinolinic acid or nicotinamide which is subject to glycine conjugation to produce nicotinuric acid.

In the kynurenine pathway, tryptophan is converted by two sequential enzymatic reactions to kynurenine. Kynurenine is then converted either to kynurenic acid by the enzyme kynurenine transaminase, or to 3-hydroxykynurenine by the enzyme kynurenine hydroxylase. The enzyme kynureninase then converts 3-hydroxykynurenine to 3-hydroxyanthranilic acid, an intermediate in the production of the excitotoxin quinolinic acid. Indeed, substrate nonspecificity of the mammalian enzyme kynureninase (EC 3.7.1.3) is documented in the literature. Besides the two natural substrates already listed, other naturally occurring and synthetic substrates exist. For example, kynureninase also splits some γ-oxy-aliphatic amino acids as well as some γ-oxy-phenyl amino acids (Wiss O. and Fuchs H., *Experientia,* 12:472–473, 1950). It is this nonspecificity of the enzyme which may be used to therapeutic advantage by the design of drugs as potential substrates.

inhibitor of both kynurenine hydroxylase and kynureninase. As a substrate for the enzyme kynureninase, nicotinylalanine is itself converted to nicotinamide. Decker R. H., et al., *J. Biol. Chem.,* 238:1049–1053, 1963.

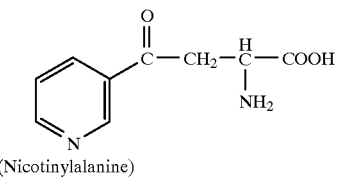

(Nicotinylalanine)

(I)

Nicotinylalanine has an asymmetric carbon atom and accordingly exists in enantiomeric (2R and 2S) or racemic forms. Inhibition of the kynurenine hydroxylase and kynureninase enzymes not only reduces production of the

THE KYNURENINE PATHWAY

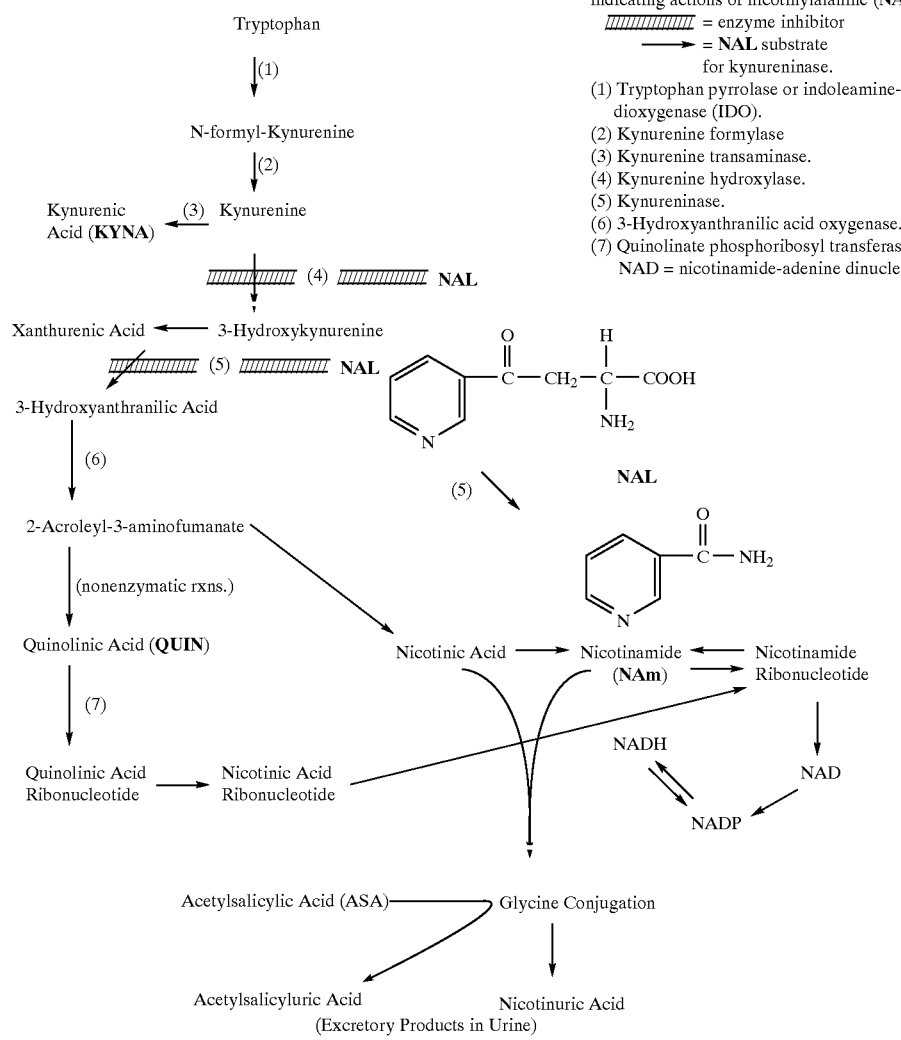

Nicotinylalanine (also referred to as γ-(3-pyridyl-γ-oxo-α-aminobutyrate; M. W.=194.1 Daltons) (Formula I)) is an excitotoxin quinolinic acid, but also increases the synthesis of kynurenic acid, a compound capable of inhibiting the effect of quinolinic acid. Decker, R. H., et al., *J. Biol. Chem.*, 238:1049–1053, 1963; Moroni, F., et al., *J. Neurochem.*, 57:1630–1635, 1991.

This enzyme-inhibitory activity of nicotinylalanine is discussed as the basis for the use of nicotinylalanine to protect against the neurotoxicity associated with metabolism of tryptophan and production of quinolinic acid in Pellicciari, R., et al., International application WO 91/17750.

Despite the use of nicotinylalanine to reduce toxicity associated with quinolinic acid, new methods and compositions are still needed to provide more effective reduction of cellular toxicity associated with poly (ADP) ribosylation reactions. Such methods and compositions are also needed to provide therapeutic increases in endogenous concentrations of nicotinamide which can effectively inhibit the activity of poly (ADP-ribose) synthetase reactions.

As a co-factor for the enzyme kynureninase, the active cellular form of B6 pyridoxal phosphate increases the rate of conversion of nicotinylalanine to nicotinamide (Takeuchi F. and Shibata Y., *Biochem. J.*, 220: 693–699, 1984). Pyridoxal phosphate (PLP) deficiency is reported to occur in viral diseases, including HIV infection and its associated complications in AIDS (Baum M. K. et al., *J. Acq. Imm. Def. Synd.*, 4:1122–1132, 1991), and in various cancers in mice (Gridley D. S. et al., *J. Natl. Cancer Inst.*, 78:951–959, 1987; Ha C. et al., *J. Nutr.*, 114:938–945, 1984) as well as in humans (Potera M. S. et al., *Am. J. Clin. Nutr.*, 30:1677–1679, 1977). General descriptions of pathological conditions in humans underlying PLP deficiency have also been reported. (Serfontein W. J., U.S. Pat. No. 5,254,572, 1993).

SUMMARY OF THE INVENTION

This invention provides methods and compositions for reducing cellular toxicity, in vitro and/or in vivo, associated with poly-(ADP)-ribosylation reactions. Specifically, the compositions of this invention comprise at least one compound of Formula II, such as nicotinylalanine, and an inhibitor of glycine conjugation associated with the metabolism of nicotinamide, and/or at least one B6 vitamin. Compounds of formula II are as follows:

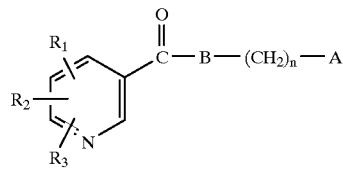

(II)

wherein $R_1$, $R_2$, and $R_3$ are independently, the same or different and may be selected from the group consisting of hydrogen, halogen, amino, nitro, hydroxyl, ethoxycarbonyl, carboxyl, carbamoyl, carbamoyloxy, and an optionally substituted $C_{1-2}$ alkyl wherein the alkyl group may be substituted with a halogen, amino, nitro, or hydroxyl group;

B is either a bond, NH or oxygen;

A is selected from —$CR_4NH_2COOH$, $CR_5R_6R_7$, and $NR_5R_6$, and wherein $R_4$ is selected from hydrogen; halogen; amino; nitro; hydroxyl; ethoxycarbonyl; carboxyl; carbamoyl; carbamoyloxy; an optionally substituted $C_{1-2}$ alkyl wherein the alkyl group may be substituted with a halogen, amino, nitro, or hydroxyl group; a side chain of a naturally occurring amino acid optionally substituted at the α carbon with H or any of a series of heterocyclic groupings, including pyridinyl, imidazolyl, phenyl, or indolyl;

and wherein $R_5$, $R_6$ and $R_7$ are the same or different and are selected from the group consisting of $C_{1-4}$ alkyl, hydrogen, and phenyl, pyridinyl, imidazolyl or indolyl; $COOCH_2R_8$ wherein $R_8$ is selected from the group consisting of phenyl, pyridinyl, imidazolyl, and indolylyl, and wherein n is 0, 1, 2 or 3.

The composition of the invention is effective for increasing cellular concentrations of endogenous nicotinamide of cells in culture or in individuals.

In another embodiment of this invention, the cellular concentration of nicotinamide is increased by providing a combination of pyridoxine hydrochloride (B6) with nicotinylalanine, a related analogue or mixture thereof, and optionally an inhibitor of glycine conjugation. The compositions are effective in vitro for cultured cells possessing the potential or actual property of an inducible kynurenine pathway. The composition is effective in vivo in a diseased state when one or more cellular elements within one or more tissues reflect an induced kynurenine pathway. In a preferred embodiment of this invention the inhibitor of glycine conjugation is aspirin.

By increasing the concentration of endogenous nicotinamide, the compositions and methods of this invention are useful for treating individuals, including humans, having at least one pathological condition for which activation of poly (ADP-ribose) synthetase is a contributory factor. Such conditions include various neurodegenerative, infectious, neoplastic, and autoimmune diseases. Specific diseases for which the compositions and methods of this invention would be expected to provide a therapeutic benefit include, for example, epilepsy, neurotoxicity associated with vascular stroke, Huntington's Disease, Alzheimer's Disease, Parkinson's Disease; a variety of viral diseases including AIDS; various cancers; and diabetes mellitus type 1.

Unlike prior attempts at increasing concentrations of nicotinamide by administering nicotinamide itself, which required high concentrations of drug, were nonspecific regarding targeting the site of action, this invention enables target specific increases in nicotinamide to be achieved using comparatively lower doses of nicotinylalanine, or an analogue thereof, and results in decreased production and activity of excitotoxic amino acids.

Furthermore, the compositions of this invention which include inhibitors of glycine conjugation and/or B6, provide further increases in cellular nicotinamide concentrations than achieved with nicotinamide or nicotinylalanine alone.

It is an object of this invention to provide compositions which decrease activity of poly (ADP-ribose) synthetase and decrease the synthesis and activity of excitotoxic amino acids.

It is another object of this invention to provide methods and compositions useful for reducing cell toxicity which is associated with poly-(ADP)-ribosylation reactions.

It is another object of this invention to provide compositions useful for reducing the cellular toxicity associated with nitric oxide.

It is another object of this invention to provide methods of treating individuals with diseases in which activation of poly (ADP-ribose) synthetase contributes to the pathogenicity.

It is another object of this invention to provide methods and compositions useful for treating or reducing the severity of various neurodegenerative diseases, diseases due to infection, autoimmune diseases and cancer in mammals, including humans.

BRIEF DESCRIPTION OF THE FIGURES

FIG. 4A: LP-BM5+PBS=virus positive, plus daily (M–F) i.p. injections of the PBS vehicle for dissolving test substances; NAL 400+ASA 20=virus positive, plus daily (M–F) i.p. injections of nicotinylalanine (400 mg/kg body weight) in combination with aspirin (20 mg/kg body weight); NAL 400+AZT=virus positive, plus daily (M–F) i.p. injections of nicotinylalanine (400 mg/kg) in combination with 3'-Azidothymidine (1 mg/mL in drinking water); virus positive, plus AZT 1.0 mg/mL=virus positive, plus 3'-Azidothymidine (1 mg/mL in drinking water).

FIG. 4B: LP-BM5+PBS=as described above; NAL 400=virus positive, plus daily (M–F) i.p. injections of nicotinylalanine (400 mg/kg) only; NAL 400 delay=nicotinylalanine (400 mg/kg) only, injected i.p. daily (M–F) beginning two weeks after virus inoculation. Since each data point represents a mean plaque value for only three mice per group sacrificed at interim monthly intervals, statistically significant differences between any groups were only apparent at the 4 month interval.

DETAILED DESCRIPTION OF THE INVENTION

Figure 1:
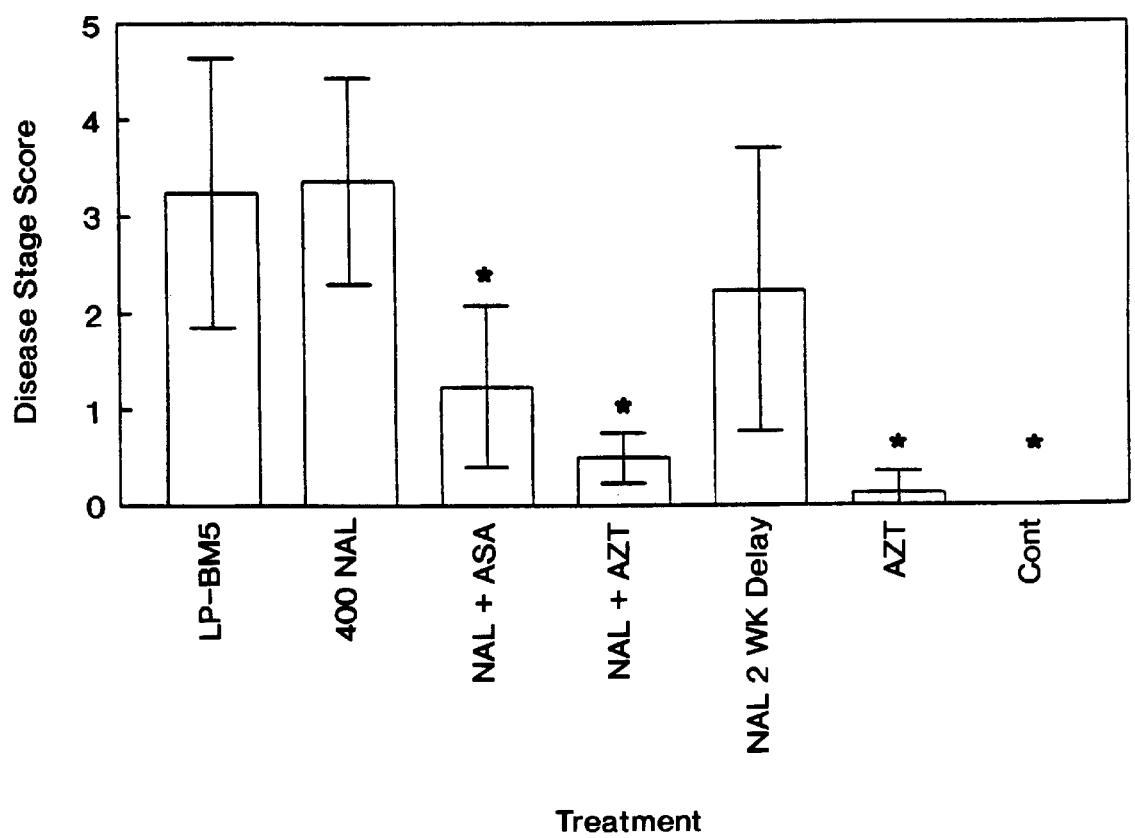
FIG. 1: Disease Stage Scores for Survival Groups of Mice Treated with Nicotinylalanine (NAL) and/or Aspirin (ASA) and/or 3'-Azidothymidine (AZT). The virus-negative control group is included, although these mice never showed any evidence of disease. Each value represents the mean and one standard standard deviation for groups of surviving mice (at least 4 mice per group) at termination of the study, following 28 weeks post-inoculation by LP-BM5 virus. Asterisks indicate statistically significant differences, as compared to the LP-BM5 vehicle-treated controls. Using independent group t-test comparisons with the LP-BM5 controls and Newman Keuls test for equality of variance, the following comparisons between group means reached statistical significance (* in Figure): NAL+ASA ($p<0.05$); NAL+AZT ($p<0.01$); AZT ONLY ($p<0.01$); Virus-negative Cont. ($p<0.001$).
Figure 2:
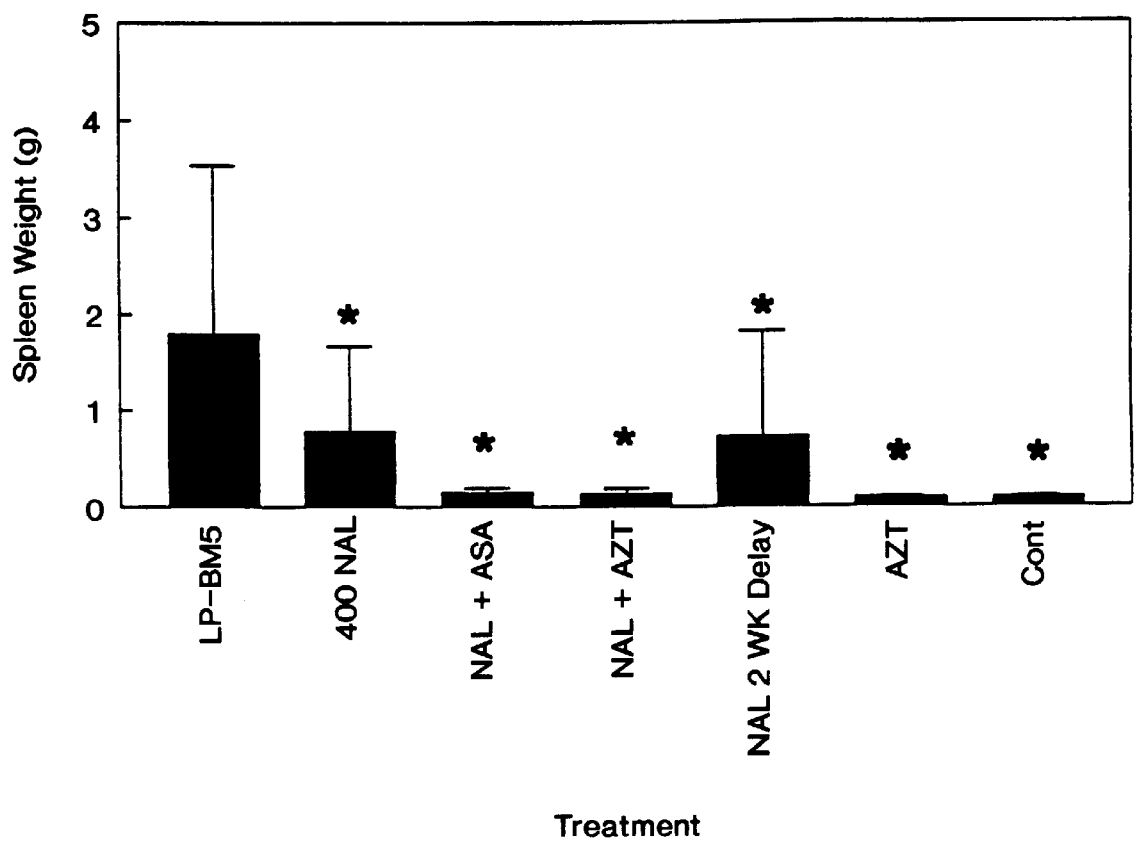
FIG. 2: Spleen Weights for Survival Groups of Mice Treated with Nicotinylalanine (NAL) and/or Aspirin (ASA) and/or 3'-Azidothymidine (AZT). The virus-negative control group is included, as a reference for normal spleen weight in this group of mice randomly selected and housed under identical conditions as the virus-inoculated experimental groups. See Legend, FIG. 1, for data representation and statistical analysis. * indicates a mean value that was statistically different from the virus-positive (LP-BM5) control group in pairwise comparisons using Newman Keuls test, $p<0.05$.
Figure 3:
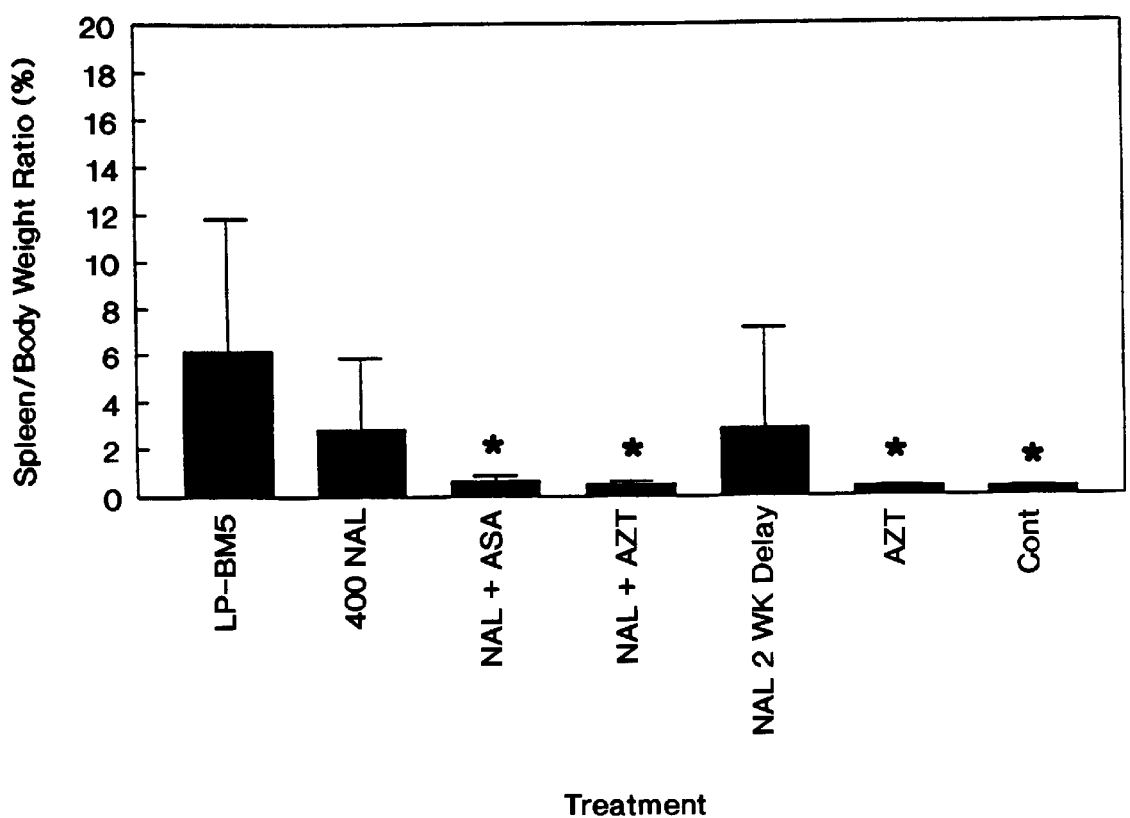
FIG. 3: Spleen to Body Weight Ratio for Survival Groups of Mice Treated with Nicotinylalanine (NAL) and/or Aspirin (ASA) and/or 3'-Azidothymidine (AZT). Values were calculated for each animal as the spleen weight divided by the body weight times 100% for each animal with at least 4 animals per group. See Legend, FIG. 1, for data representation and statistical analysis. * indicates a mean value that was statistically different from the virus-positive (LP-BM5) control group in pairwise comparisons using Newman Keuls test, $p<0.05$.

This invention relates to compositions comprising nicotinylalanine [NAL, γ-(3-pyridyl)-γ-oxo-α-aminobutyrate], or an analogue of nicotinylalanine, in combination with at least one inhibitor of glycine conjugation of nicotinamide, such as acetylsalicylic acid (ASA, aspirin) which are useful for reducing cellular toxicity by increasing endogenous concentrations of nicotinamide. In another embodiment of this invention endogenous concentrations of nicotinamide are increased by providing cells nicotinylalanine, or a related analogue, and pyridoxine hydrochloride or pyridoxal (B6), and optionally an inhibitor of glycine conjugation.

To provide sustained and increased cellular levels of pyridoxal phosphate, pyridoxal or another form of B6 purportedly can be administered chronically in oral dosages. Other methods of administering B6 may also be used with this invention and are known to those in the art. Thus, increased cellular levels of active B6 may be made available as cofactor in the kynureninase catalyzed conversion of nicotinylalanine (or its analogues) to nicotinamide.

Without being bound by theory, the methods and compositions of this invention which reduce cellular toxicity are believed to act by directly or indirectly reducing the activity of poly (ADP-ribose) synthetase or other poly (ADP)-ribosylation reactions. Cellular toxicity, in vitro or in vivo, associated with poly (ADP)-ribosylation reactions is often associated with increases in cellular nitric oxide.

Increases of cellular nicotinamide are provided according to this invention by providing to cells the compositions of this invention comprising nicotinylalanine and an inhibitor of glycine conjugation. According to this invention, cells, in vitro or in vivo, are exposed to soluble nicotinylalanine, or a suitable analogue described below, and the inhibitor of glycine conjugation. Nicotinylalanine is then endogenously converted to nicotinamide, particularly in those cells in which the kynurenine pathway is induced by cytokines and/or by mediators of disease processes. Analogues of nicotinylalanine also may be converted to nicotinamide, or to other compounds which are effective for inhibiting either or both of kynurenine hydroxylase and kynureninase and may also be substitutes for glycine conjugation and also inhibit poly-(ADP)-ribosylation reactions. In vitro, cells may be exposed to any non-toxic buffer or medium in contact with the cells. In vivo, cells are generally in contact with a physiologic fluid such as for example, blood, plasma, lymph, cerebral spinal fluid, or interstitial fluid. Although the beneficial effects of this invention are believed to occur at a cellular level, the methods and compositions of this invention may also result in detectable increases of the concentration of nicotinamide present in plasma. Such increases may be used to monitor the effectiveness of the compositions and methods of this invention for increasing nicotinamide and the adequacy of specific dosing protocols.

The methods and compositions of this invention are useful for reducing cellular toxicity of cells in vitro or in vivo which possess the potential or actual property of an inducible kynurenine pathway. Examples of such cells include, but are not limited to cells of the monocyte/macrophage lineage, or cells of a transformed (e.g. cancer cell) lineage.

The methods and compositions of this invention which reduce cellular toxicity are also useful as treatments for diseases in animals, including humans, which are responsive to nicotinamide (niacinamide) treatment. Disease classifications known, or thought potentially, to be responsive to nicotinamide therapy include: (1) neurodegenerative diseases in which nitric oxide mediates the excitotoxic cell death of glutamate or related excitotoxins such as quinolinate (e.g., some forms of epilepsy, neurotoxicity associated with vascular stroke, Huntington's Disease, some forms of Alzheimer's Disease, some forms of schizophrenia and some forms of Parkinson's Disease); (2) a variety of infectious diseases including bacterial or viral diseases in which activation of cellular immunity and the inflammatory response involving macrophages characterize a chronic state of the disease process (e.g., Acquired Immune Deficiency Syndrome, AIDS); (3) various cancers in combination with radiation therapy; and (4) diabetes mellitus type 1 (insulin-dependent diabetes mellitus, IDDM).

The therapeutic significance of the general application of this invention relates to the relative potency of nicotinamide (NAm) as an inhibitor of poly-(ADP)-ribosylation reactions (PARS) and poly-(ADP-ribose) polymerase (PARP). As discussed above, a variety of pathologic conditions are related to DNA damage resulting from inappropriate activation of poly (ADP-ribose) synthetase, which may occur in response to increases in nitric oxide.

Compositions of the invention comprise nicotinylalanine and a glycine inhibitor suitable for decreasing the glycine conjugation of nicotinamide associated with its metabolism. Conjugation in the liver and kidney with glycine is an important mechanism for excretion of various carboxylic acids—both natural biochemical metabolites and drugs (Hutt A. J. & Caldwell, J. In: *Conjugation Reactions in Drug Metabolism*, Mulder, G. J., editor, 1995, p. 273–305. As discussed below, conjugation as part of the kynurenine pathway is not limited to the liver or kidney cells. In the kynurenine pathway, nicotinic acid may be converted either to nicotinamide or, via glycine conjugation, to nicotinuric acid. Inhibition of glycine conjugation therefore enhances nicotinamide by both directly reducing nicotinamide metabolism as well as increasing the synthesis from nicotinic acid. This effect can be seen even in the absence of cytokine-induced kynurenine metabolism and is enhanced by increasing the dose from about 20 to about 100 mg/kg of the glycine conjugation inhibitor, aspirin, as shown in Table 1.

In addition to nicotinylalanine, which is preferred, other structurally related analogues as defined by formula II below are suitable for use in this invention provided that they either directly or indirectly inhibit or decrease the activity of kynurenine hydroxylase and kynureninase and are capable of causing, either directly or following some degree of metabolism, the inhibition of poly (ADP-ribose) synthetase.

Compounds of formula II are as follows:

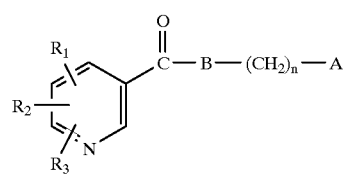

(II)

wherein $R_1$, $R_2$, and $R_3$ are independently, the same or different and may be selected from the group consisting of hydrogen, halogen, amino, nitro, hydroxyl, ethoxycarbonyl, carboxyl, carbamoyl, carbamoyloxy, and an optionally substituted $C_{1-2}$ alkyl wherein the alkyl group may be substituted with a halogen, amino, nitro, or hydroxyl group;

B is either a bond, NH or oxygen;

A is selected from —$CR_4NH_2COOH$, $CR_5R_6R_7$, and $NR_5R_6$, and wherein $R_4$ is selected from hydrogen; halogen; amino; nitro; hydroxyl; ethoxycarbonyl; carboxyl; carbamoyl; carbamoyloxy; an optionally substituted $C_{1-2}$ alkyl wherein the alkyl group may be substituted with a halogen, amino, nitro, or hydroxyl group; a side chain of a naturally occurring amino acid optionally substituted at the α carbon with H or any of a series of heterocyclic groupings, including pyridinyl, imidazolyl, phenyl, or indolyl;

and wherein $R_5$, $R_6$ and $R_7$ are the same or different and are selected from the group consisting of $C_{1-4}$ alkyl, hydrogen, and phenyl, pyridinyl, imidazolyl or indolyl;

COOCH$_2$R$_8$ wherein R$_8$ is selected from the group consisting of phenyl, pyridinyl, imidazolyl, and indolylyl, and wherein n is 0, 1, 2 or 3.

Compositions of the invention may also comprise mixtures of nicotinylalanine or at least one of the analogues described above. Since the embodiment of the invention is to generate enhanced nicotinamide levels in cells, while inhibiting formation of excitotoxins of the kynurenine pathway, it will be recognized that at least two general classes of compounds 3-pyridyl-carboxylates wherein B is a bond, or 3-pyridyl-carboxamides wherein B is NH may satisfy these conditions as a general principle.

For the 3-pyridylcarboxylates preferred compounds are wherein R$_1$, R$_2$ and R$_3$ are selected from hydrogen, methyl, ethyl, halogen, amino, nitro, hydroxyl, ethoxycarbonyl, carboxyl, carbamoyl, carbamoyloxy; A represents an alkyl-α-amino carboxylic acid bound to B or (CH$_2$)$_n$ by the α carbon optionally substituted at the α carbon with H or any of a series of heterocyclic groupings, including pyridinyl, imidazolyl, phenyl, or indolyl, and n is 0, 1, 2, or 3.

Examples of analogues of nicotinylalanine which relate to the inhibition of cellular toxicity as described by the invention, and which are suitable for use in this invention are wherein R$_1$, R$_2$ and R$_3$ are as defined above, n is 0, 1, 2 or 3, and A is selected from the group consisting of glycinyl, alanyl (nicotinylalanine), methoxyalanyl (nicotinylmethoxyalanine), γ-methyleneglutamate,, orthinine, arginine or lysine, serine, threonine, or valine, leucine and isoleucine.

Examples of preferred aromatic substitutions with the desired activity occur wherein n is 0, 1, 2 or 3, and A is selected from the group consisting of glycinyl, optionally substituted with pyridine-3-carboxylic acid or pyridine-2,3-carboxylic acid, phenylalanine, tyrosine, tryptophan and histidine.

Useful analogues may be prepared according to methods disclosed in the literature (Iselin B. M., et al., *J. Am. Chem. Soc.* 72:1729–1731, 1950; Sperber N. et al., *J. Am. Chem. Soc.* 72:2012–2015, 1950) when n is 1 or 2, and A is alanyl; methoxyalanyl; γ-methyleneglutamate; orthinine, arginine or lysine; serine, threonine, or valine; leucine or isoleucine.

Synthesis of 3-pyridinemonocarboxylic acid, nicotinic acid and its amide nicotinamide (niacinamide) is described in—e.g., Oliveto E. P., Pyridinecarboxylic Acids. In: *Pyridine and Its Derivatives, Part Three*, Klingsberg E., Editor, Interscience Publishers, 1962, pp. 179–346, which is incorporated herein by reference. The natural existence and/or synthesis of many other analogues of nicotinylalanine are reviewed by Godfrey J. C., Pyridine side-chain carboxylic acids, also In: *Pyridine and Its Derivatives, Part Three*, Klingsberg E., Editor, Interscience Publishers, 1962, pp. 347–509, which is also incorporated herein by reference.

Examples of other analogues of nicotinylalanine and their methods of synthesis are described in the references below which are also incorporated herein by reference:

(1) β-Pyridyl Carbinol Nicotinoyl Glycinate (U.S. Pat. No. 3,770,753);

(2) D-Glucose-1-0-Nicotinoyl-2-Deoxy-2-Nicotanamido Derivatives (U.S. Pat. No. 3,950,324);

(3) Certain Substituted Picolinoyl, Nicotinoyl and Isonicotinoyl Hydrazones (U.S. Pat. No. 3,503,987);

(4) Lysergic Acid N-Nicotinoyl Piperazide (U.S. Pat. No. 3,752,815);

(5) 2-Diethylamino-ethyl Nicotinate Para-Chlorophenoxy-isobutyric acid salt. (U.S. Pat. No. 3,717,649);

(6) "Lyspamin and other new derivatives of nicotinic acid." H.Suter. Schweiz. med. Wochschr. 78, 853–855, 1948. *Chem. Abstracts*, Vol. 48, 3360 c;

(7) "Synthesis of some derivatives of nicotinic acid." I. B. Simon. *Zhur. Obschei Khim.* 21, 1537–1540, 1951, Chem. Abstracts, Vol. 46, 2522 d;

(8) "Substituted nicotinamides." A. Calo and V. Evdokimoff. *Gazz. chim. ital.* 80, 456–470, 1950. Chem. Abstracts, Vol. 45, 4243–4244.

Various inhibitors of glycine conjugation are suitable for use in the compositions of this invention. Although benzoic acid is eliminated exclusively via conjugation in the form of benzoylglycine (i.e., hippuric acid) in both humans and rodents (Bridges J. W., et al., *Biochem J.* 118:47–51, 1970) and is suitable for use in the compositions of this invention, the preferred embodiment of this invention uses aspirin (sodium acetylsalicylic acid) as a substrate of the mitochondrial glycine conjugation enzyme system since up to 75% of aspirin is conjugated to form salicyluric acid (see, kynurenic pathway) in humans (Levy G., *J. Pharm. Sci.*, 54:959–967, 1965). It will also be noted that aspirin is easily administered, widely used, and of low toxicity in humans. Several other inhibitors of glycine conjugation also suitable for use in this invention include, for example, sodium benzoate, sodium phenylacetate, sodium 1-napthylacetate, sodium isovalerate, and bromosulfophthalien (BSP). Preferred inhibitors of glycine conjugation include aspirin, sodium benzoate, and sodium phenylacetate. Aspirin is most preferred.

As described above, in another embodiment of this invention, vitamin B6, or another substance capable of increasing plasma concentrations of B6, in combination with nicotinylalanine, and/or a related analogue and optionally an inhibitor of glycine conjugation is used to increase nicotinamide concentrations. Various sources of B6 including pyridoxal are described in Serfontein U.S. Pat. No. 5,254,572 which is incorporated in its entirety herein by reference.

The compositions and treatments of this invention are effective for increasing the concentration of nicotinamide above those achieved by the administration of nicotinylalanine alone. This is demonstrated in the examples (see Table 4) in retrovirus-infected (MAIDS) mice. Potentiation by aspirin is due to the fact that both nicotinic acid (an immediate precursor to nicotinamide) and aspirin are degraded by glycine conjugation. The presence of aspirin acts as a competitive inhibitor of nicotinic acid degradation (Ding R. W., et al., *Clin. Pharmacol. Ther.* 46:642–647, 1989). Although large exogenous doses of nicotinamide are metabolized to N-methylnicotinamide and pyridone carboxyamide metabolites, observations in rodents that approximately 16% of nicotinamide is converted to nicotinuric acid are consistent with some metabolism of nicotinamide by glycine conjugation. (Shibata K., *J. Nutr.*, 119:892–895, 1989). Therefore, our observed enhancement of nicotinamide levels in mouse tissues following combined nicotinylalanine and aspirin administration is likely due to a combined competitive inhibition of glycine conjugation degradation of nicotinic acid and nicotinamide.

The utility of a combination treatment using the composition of this invention, consisting of for example nicotinylalanine and aspirin is believed to result from an enhancement of cellular nicotinamide levels which then act as natural inhibitors of poly(ADP-ribose) synthetase and related poly(ADP)-ribosylation reactions.

The methods and compositions of this invention are particularly advantageous because they provide a means of targeting drug action to specific tissues involved in the disease process. Activation of specific enzymes in the kynurenine pathway, particularly, indoleamine-2,3-dioxygenase (IDO), and subsequently kynurenine hydroxylase and kynureninase (3-hydroxykynureninase) occurs as a consequence of various disease processes. Heyes, M. P., et al., *J. Neuroimmunol.,* 40:71–80, 1992; Heyes, M. P., et al., *Biochem. J.,* 283:633–635, 1992; Werner, E. R., et al., *Life Sci.,* 41:273–280, 1987; Sardar, A. M., et al., *J. Neurochem.,* 64:932–935, 1995. By providing a competitive substrate for the kynurenine hydroxylase and kynureninase enzymes, the production of excitotoxic amino acids is reduced and the synthesis of nicotinamide an inhibitor of poly(ADP-ribose) synthetase, another enzyme activated in pathologic cells, is increased.

As discussed above, the methods and compositions of this invention are useful for reducing poly-(ADP)-ribosylation reactions which may be activated by nitric oxide, or other substances, contribute to cellular toxicity and are associated with various types of diseases. Thus, this invention could reasonably be expected to be useful in the treatment of any disease having a pathology resulting from, at least in part, poly(ADP)-ribosylation reactions. Such diseases include neurodegenerative diseases, infectious diseases, autoimmune and neoplastic diseases.

Existing drugs useful in the treatment of diseases as listed above have varying degrees of therapeutic efficacy, though none are curative. Such therapeutic agents could have additive or synergistic effects when combined with compositions of this invention, particularly if the mechanisms of action of the existing or other drugs is different from the mechanism by which the compositions of this invention exert their activity.

For example, 3'azido-3'deoxythymidine (AZT) and its analogues, which act as retroviral reverse transcriptase inhibitors, are useful agents in the treatment of HIV-1 infection and AIDS and could be used in combination with the compositions of this invention. The value of these combinations is provided in the Examples, wherein nicotinylalanine in combination with AZT has equal or better efficacy than AZT alone in the treatment of retrovirally infected mice. Such combinations are particularly useful as nicotinylalanine does not potentiate toxic effects of AZT. Based on this invention, nicotinylalanine in combination with inhibitors of glycine conjugation and/or in combination with vitamin B6, or another substance capable of increasing B6, would also be expected to have efficacy in combination with AZT.

The neurodegenerative diseases for which this invention would be particularly useful are those in which the neurodegenerative component depends, at least in part, upon excitotoxic pathogenic mechanisms. Examples of such diseases are reviewed in Bruhyler J., et al., *Neurosci. Behav. Rev.,* 17:373–384 (1993) and Coyle, J. T., et al., *Science. USA,* 262:689–700 (1993) and include, for example, various forms of epilepsy, Huntington's disease, Parkinson's disease, Alzheimer's disease and stroke.

In one embodiment, the compositions and/or methods of this invention are used to treat individuals infected with virus and in whom the viral infection has resulted in activation of poly(ADP-ribosylation) reactions. For example, targeting increases in nicotinamide to HIV-infected cells could be achieved by relying on the induction of the tryptophan pathway in activated macrophages. As reviewed by Fuchs D., et al. (*Immunology Today,* 9:150–155, 1988), many reports have established that human macrophages infected with HIV-1 are in a state of chronic immune activation due, at least in part, to sustained elevations of circulating macrophage activating factor (interferon-gamma; a multifunctional cytokine). An analogous state of chronic immune activation exists for mouse macrophages infected with LP-BM5 murine leukemia virus yielding murine acquired immune deficiency syndrome or MAIDS (Kort J. J. and Eiseman J. L., *Can. J. Inf. Dis.,* 3:115B–122B, 1992). Importantly, HIV-1-infected macrophages are a major reservoir of virus and are thought to play a prominent role in pathogenesis of AIDS (Mosier D. and Sieburs H., *Immunology Today,* 15:332–339, 1994). In regard to cytotoxic phenomena associated with activated macrophages, including brain microglial cells, it should be noted that interferon-gamma in combination with other cytokines also induces nitric oxide production which then mediates a variety of cellular injuries and cell death (Lorsbach R. B., et al., *J. Biol. Chem.,* 268:1908–1913, 1993; Chao C. C., et al., *J. Immunol.,* 149:2736–2741, 1992.

One function of the interferon-gamma (IFN-γ) effect upon macrophages is to induce the rate-limiting enzyme in tryptophan metabolism through the kynurenine pathway—namely, indoleamine 2,3-dioxygenase (IDO) (Fuchs D., et al., *J. Interferon Res.* 10, 599–603, 1990; Takikawa O., et al., *J. Biol. Chem.,* 263:2041–2048, 1988; reviewed in Taylor M. W. and Feng G., *FASEB J.,* 5, 2516–2522, 1991). As seen in the metabolism of tryptophan through the kynurenine pathway, induction of IDO by endogenously released IFN-γ in persons infected with HIV-1 results in progressively elevated levels of quinolinic acid (QUIN) in serum and cerebrospinal fluid (CSF) and these levels correlate with progression (Stages) of the disease (Fuchs D., et al., 1990, ibid) and also with severity of the so-called AIDS encephalopathy (Heyes M. P., et al., *Ann. Neurol.,* 29:202–209, 1991). A precise function remains unknown for these logarithmic increases in QUIN levels (see, e.g., review by Spencer D. and Price R. W., *Microbiol. Revs.,* 46, 655–693, 1992). However, the molecular flux through the kynurenine pathway to QUIN increases from 10 to 1000 times normal levels in serum and CSF as a result of chronic cellular immune activation due to release of endogenous stores of IFN-γ (Fuchs D., et al., 1990, ibid; Heyes M. P., et al., 1991; ibid).

This invention utilizes this substantially enhanced molecular flux in the kynurenine pathway and the fact that nicotinylalanine, and related analogues, act as an antimetabolite to produce many-fold increases of intracellular nicotinamide in macrophages. Thus, for example, intraperitoneal injections of nicotinylalanine (200–400 mg/Kg) in combination with aspirin (20 mg/Kg) into retrovirus-infected C57BL6 mice substantially enhance blood and tissue nicotinamide levels. Metabolic relationships are illustrated in the Kynurenic pathway chart.

In addition to AIDS and neurologic diseases, other conditions would be expected to benefit from nicotinamide pharmacotherapy. These include treatments of various tumors in combination with carbogen or with radiation therapy (Dorie M. J., et al., *Int. J. Radiat. Onc. Biol. Phys.,* 28, 145–150, 1994) and in the prevention of insulin-dependent diabetes mellitus (IDDM) (Elliott R. B., et al., *Ann. NY Acad. Sci.,* 696, 333–341, 1993). Mechanisms by which nicotinamide enhances radiation or carbogen (95% $O_2$–5% $CO_2$) damage to human tumors may be related to increased blood flow to the tumors (Lee I. & Song C. W., *Rad. Res.,* 130:65–71, 1992; Dorrie M. J., et al., *Int. J. Rad. Oncol. Biol. Phys.,* 28:145–150, 1994) or could be due to protection of normal cells from NAD depletion due to radiation or carbogen induced DNA strand breaks resulting in activation of poly(ADP-ribose) polymerase reactions (Ben-Hur E., et al., *Cancer Res.,* 45:2123–2127, 1985). In the pathogenesis of IDDM, there is evidence for activated macrophages in destruction of pancreatic islet cells with toxicity being prevented by injection of nicotinamide as a vitamin (Kallman B. V., et al., *Life Sci.*, 51, 671–678, 1991). Since nicotinylalanine specifically enhances nicotinamide synthesis within activated macrophages, the antidiabetogenic effects of nicotinylalanine should be more potent and more specific than parenteral administration of the vitamin.

As a general response to tumors, in all neoplastic diseases studied to date, there is chronic activation of cellular immunity including induction of the kynurenine pathway in macrophages (Fuchs D., et al., 1990, supra; Taylor M. W. and Feng G., 1991, supra). In addition to induction of this pathway in macrophages, studies of numerous cell lines from a variety of animal and human cancers have also documented induction of this pathway in many but not all clonal cell lines propagated from the cancers (Taylor and Feng, supra; Leung B. S., et al., *Cancer Lett.*, 66, 77–81, 1992). The cell lines in which the kynurenine pathway is induced are generally characterized by high activity of the rate-limiting enzyme in the pathway, namely indoleamine 2,3-dioxygenase or IDO (see Pathway; Taylor and Feng, supra; Leung et al., supra). Since growth properties of cells depend upon metabolism of NAD and nicotinamide (see, e.g., Johnson G., *Eur J. Biochem.*, 112, 635–641, 1980), this invention is particularly useful for enhancing nicotinamide synthesis in those cells in which the kynurenine pathway is induced.

Depending upon whether nicotinamide is acting as a precursor of NAD or as an inhibitor of poly (ADP)-ribosylation reactions, the compositions and methods of this invention can protect against cell death (e.g., cells in which nicotinamide or NAD become limiting); or provide a means of limiting cell growth (e.g., cells in which induction of poly (ADP)-ribosylation reactions contribute to increased cell proliferation).

We have made use of this induction of the kynurenine pathway to enhance the synthesis of nicotinamide by providing nicotinylalanine, or related analogue, as an antimetabolite in the kynurenine pathway. Accordingly, nicotinylalanine is useful as a prodrug because it is metabolized to nicotinamide and inhibitors of glycine conjugation such as aspirin act to further enhance nicotinamide levels by preventing degradation of nicotinic acid (see Pathway) and to some extent preventing degradation of nicotinamide itself.

In summary, many neurodegenerative, infectious, neoplastic, and autoimmune diseases have in common the induction of poly.(ADP-ribose) synthetase and enhanced levels of ADP-ribosylation reactions. Some of these ribosylation reactions may have functional significance for the invading pathogen (e.g., post-transcriptional modification of HIV-1 proteins) but many are of unknown significance to pathogen or host response. However, sustained activation of these ribosylation reactions can lead to depletion of NAD stores and cell death. All of these reactions, including the induction of poly(ADP-ribose) synthetase, are inhibited by nicotinamide. This invention provides novel compositions and methods using an established drug (nicotinylalanine, or related analogue) with little known toxicity in order to substantially enhance tissue and cellular levels of nicotinamide, and thereby modulating cell function and the chronicity and severity of these diseases. This invention also provides effective levels of kynurenic acid (KYNA) as an NMDA receptor antagonist, while concurrently lowering pathologic levels of the excitotoxins, quinolinic acid and 3-hydroxykynurenine.

For therapeutic use in man, the increase in endogenous nicotinamide levels following nicotinylalanine, or related analogue, treatment will obviate the less effective treatment with exogenous (oral or injectable) nicotinamide and will provide a more directed increase in nicotinamide at tissue and cellular sites of disease and or inflammation. As discussed above, these benefits of nicotinylalanine treatment are applicable to other diseases besides neurodegeneration. R. H. Decker, et al. (ibid) reported a 4–5 fold increase in N-methylnicotinamide levels in the urine of rats treated with nicotinylalanine. Since N-methylnicotinamide is a major urinary excretion product of nicotinamide in the rat, increases in the endogenous levels of nicotinamide following nicotinylalanine injection are at least 5 fold.

For its proposed in vitro and in vivo applications, nicotinylalanine (NAL) preferably is administered as the 2S isomer, as the free base or as one of its physiologically equivalent derivatives (salts, esters, non-toxic amides) in combination with the glycine conjugation inhibitor, and/or B6 or another substance which causes an increase in B6. In the preferred embodiment, the nicotinylalanine and glycine conjugation inhibitor are administered together as a single formulation, however this invention also includes their separate administration both as individual formulations and at different times. To obtain the fullest benefit of the B6, glycine conjugation inhibitor and nicotinylalanine in therapeutic applications it is preferable to administer them so their peak plasma concentrations occur concurrently. Since both aspirin and nicotinylalanine have similar drug kinetic characteristics, it is most preferred to administer this combination as a single admixture.

Results from studies in a mouse model of AIDS (i.e., the LP-BM5 strain of murine leukemia virus-induced murine acquired immunodeficiency syndrome, MAIDS) are consistent with efficacy of a parenteral dose in humans of nicotinylalanine (isomer) between about 100 and 200 mg/kg body weight per day in combination with aspirin at about 20 mg/kg per day. Chronic (i.e., daily, Mon.–Fri., for more than four month duration) intraperitoneal injections of racemic NAL (400 mg/kg) into C57BL/6 mice (MAIDS Study) have not been associated with obvious behavioral toxicity. Also, an acute dose of 500 mg/kg of a racemic mixture of NAL has been reported not to result in any behavioral effects in rats. Connick J. H., et al., *Gen. Pharmac.*, 23:235–239, 1992. Chronic doses of nicotinamide (NAm) of up to 3.0 grams per day for 6 to 12 months in clinical studies of diabetes in humans have been reported without any significant side effects. Vague P., et al., *Lancet*, I:619–620, 1987. This is consistent with the lack of toxicity reported for NAm in other human studies. (Hoffer A., *Schizophrenia*, 1:78–87, 1969).

Depending upon a patient's condition and diagnosis, nicotinylalanine, or its physiological equivalent, may be administered in doses between about 10 and 200 mg/kg total dose/day as the active (2S) isomer. Accordingly, for humans preferred median-effective divided doses which could be administered by mouth would be equivalent to approximately 1800 mg Q.I.D. for a 70 kg person in combination with 650 mg (10 grains) of aspirin. This is similar to single doses of nicotinamide given orally to cancer patients of 6000 mg (6 grams) in combination with radiation (Stratford and Dennis, 1992, ibid).

For other diseases in which nicotinylalanine is proposed to act as a precursor to enhance levels of relevant pools of nicotinamide, dosages are expected to be similar to the above or lower depending upon the patient's condition and the nature and severity of the disease. Guidelines for selection of dosages, combinations, and intervals will depend, in part, upon results from efficacy trials of nicotinamide in current human studies.

Synthesis of 2S, 2R-(racemic) Nicotinylalanine: Synthesis of the racemic mixture of nicotinylalanine may be achieved according to the method of Decker, R. H. et al. (1963), supra, as modified from the synthetic scheme for hydroxycotinine described by McKennis H. Jr., et al. (*J. Org. Chem.* 28, 383–388, 1963). Briefly, bromomethyl 3-pyridyl ketone as the hydrobromide (I) is condensed with sodioacetamido-malonic ester (II) to yield 2-nicotinylmethyl 2-acetamidonmalonic ester (III). In one embodiment, tetrahydrofurane (THF) is used in this malonic ester condensation, since it dissolves the sodium derivative (II) and enhances the yield of III as contrasted to toluene alone. The resulting 2-nicotinylmethyl 2-acetamidomalonic ester (III) upon basic hydrolysis yields $\gamma$-(3-pyridyl)-$\gamma$-oxo-$\alpha$-acetamidobutyric acid (IV) which, upon hydrolysis in 6N HCl, yields $\gamma$-(3-pyridyl)-$\gamma$-oxo-$\alpha$-aminobutyric acid (racemic, 2R,2S-nicotinylalanine; nicotinylalanine). Although current biologic experiments make use of the racemic dihydrochloride salt of nicotinylalanine, the natural L steric configuration (2S) is preferred (Decker, et al., 1963, supra) and tartaric acid methods for resolution of the dextrorotary 2S product are suitable for resolving the pure isomer.

The compositions of this invention comprise nicotinylalanine, or a related analogue as described above, or a mixture thereof, and, either or both B6 and the inhibitor of glycine conjugation in an amount such that their combined effect increases the concentration of cellular or plasma nicotinamide. An increase in nicotinamide concentration of any tissue including blood, plasma or urine or organ may be used to monitor the effect of treatment in accordance with this invention. Any increase in nicotinamide concentration above control levels as a result of administering the composition of this invention are within the scope of this invention. The concentration of nicotinamide present in the tissue monitored should be, or be directly proportional to a therapeutically effective amount. In accordance with this invention, tissue nicotinamide concentrations as reflected in plasma of between about 0.5 and 20 nM/ml could be expected to be therapeutic. Preferred concentrations are between about 1.0 and 10.0 nM/ml; and more preferred concentrations are between about 2.0 and 5.0 nM/ml.

The pharmaceutical composition of this invention is formulated to provide therapeutically effective amounts of the components and is effective for increasing the concentration of endogenous nicotinamide in an individual administered the composition as discussed above. Preferably such compositions comprise between about 0.5 and about 5.0 grams nicotinylalanine and between about 0.2 and about 2.0 grams aspirin. More preferably the compositions comprise between about 1.0 and about 4.0 grams nicotinylalanine and between about 0.5 and about 1.5 grams aspirin. Most preferred is about 1.0 gram nicotinylalanine and about 0.5 grams of aspirin. Dosages may be modified or adapted by methods known to those skilled in the art dependent on whether an analogue of nicotinylalanine is used. The dosage schedule of this component, if administered orally, could be two tablets Q.I.D., preferably taken with food. Therefore, the daily dosage of the most preferred composition should yield blood plasma levels for nicotinylalanine of preferably between about 200 to 1000 nmoles/ml plasma and for aspirin of between about 100 and 200 nmoles/ml plasma, respectively. However, in this combined formulation for chronic dosage schedules, plasma levels of ASA will need to be monitored and possibly corrected since the conjugation of ASA by glycine is capacity-limited (i.e., saturable) and since there is also evidence that ASA may induce its own metabolism in humans (reviewed in Hutt A. J. & Caldwell J., 1990, pp. 294–296, ibid). Therefore, although NAL and NAm appear to have little toxicity associated with nearly millimolar blood levels, the relative effective dose of ASA may require careful monitoring. B6 is preferably administered at a dose of about 0.2–1.0 mg/kg (when administered as the hydrochloride salt). Depending upon the B6 vitamin (PL, PM, or PLP) and route of administration, dosages for children and adults range from 0.03–7.2 mg/kg body weight.

The method of increasing nicotinamide may be optimized according to this invention by taking advantage of the effect of the route of administration on kinetic and bioavailability characteristics of nicotinylalanine. Nicotinylalanine administered orally has a t½ of about 60 minutes compared to only about 40 minutes and 25 minutes when administered i.v. or i.p., respectively (FIGS. 7 and 8; Table 5). Bioavailability is apparently greater however when the i.p. route is used compared to either the i.v. or oral routes. Based on these surprising results it may therefore be preferable to use both oral and i.p. routes of administration in the same individual so that their actions can act concurrently.

The pharmaceutical composition of this invention may also comprise adjuvant substances and carriers. The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone, fillers, for example lactose, sugar, maize-starch, calcium phosphate, sorbitol or glycine; disintegrants, for example starch, polyvinylpyrrolidone, sodium starch glycolate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia; non-aqueous vehicles (which may include edible oils), for example almond oil fractionated coconut oil, oily esters such as esters of glycerine, propylene glycol, or ethyl alcohol; preservatives, for example methyl or propyl p-hydroxybenzoate or sorbic acid; and if desired conventional flavoring or coloring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

EXAMPLES

Example 1 - Metabolic Studies

Methods used in Metabolic Studies: High pressure liquid chromatography (HPLC) was used to determine blood plasma levels of nicotinamide and metabolites, according to the method of Stratford and Dennis, 1992, ibid). The concentration of nicotinamide and its major metabolites were determined by comparison of peak area ratios of the unknown versus internal standard (6-methylnicotinamide, Sigma Chemical Company) to the standard curves run in control mouse blood plasma. Nicotinylalanine and at least one of its metabolic products was also found to be separated and quantified by this HPLC method.

Mice (C57BL/6 females, approximately 18 to 22 grams) were housed in microisolator cages for one week prior to the study and then randomized into treatment groups with 8 animals in each group. Preformulation protocols for preparation of parenteral administration of the NAL-ASA combination into mice have followed guidelines outlined in *Remington's Pharmaceutical Sciences Handbook,* 18th Edition, A. R. Gennaro, Editor, Mack Publishing Co., Easton, Pa., 1990. Mice were treated with racemic nicotinylalanine alone (400 mg/kg) or in combination with acetyl salicylic acid (ASA) at a dose of either 20 mg/kg or 100 mg/kg body weight. Mice were administered the drug composition in 0.02 ml/g body weight of nicotinylalanine dihydrochloride (27.4 mg/ml) intraperitoneally and the pH of the solutions were adjusted to between 6.8 to 7.4. Control mice received the vehicle for the drug compositions, being phosphate buffered saline (PBS), at the same volume on the same dose schedule as the drug-treated mice. Chronic dosing was performed daily for two weeks, Monday through Friday, and one group of mice received only a single (acute) dose of nicotinylalanine. All mice were killed two hours after their final dose and blood was collected by cardiac puncture and stored on ice, until centrifugation in a microfuge at 10,000 rpm to obtain plasma.

Plasma was frozen at −70° C. until analysis as follows: 20 nmol 6-methylnicotinamide (Sigma Chemical Corp., St. Louis) was added to each 100 μl of plasma and mixed; 1.0 ml of methanol was added and each sample was vortexed for 10 seconds; then the samples were centrifuged at 1500×G for 10 minutes and the supernatants were dried under nitrogen and reconstituted in between 100 to 250 gl of water and 25 gl of each aqueous sample was injected into the HPLC, following the method of Stratford and Dennis (1992, ibid), using, however, a Hewlett Packard 1090M chromatography system with UV detection at 260 nm. The Hypersil BDS-C18 (5 μm), 250×4 mm column was maintained at 30° C. and had a Hypersil guard column, both from Hewlett Packard Company. The mobile phase, solvents, and gradients for the plasma samples were essentially the same as described by Stratford and Dennis (1992, ibid).

Concentrations of nicotinamide, nicotinamide-oxide, 1-methyl-nicotinamide, and nicotinylalanine extracted from 90% methanol, dried under $N_2$, and reconstituted in water as above were determined by comparison of the peak area ratios of the unknown vs. the internal standard to the standard curve. Concentrations of the unidentified nicotinylalanine metabolite (NAL-X) were determined in the same way as above, except peaks were compared to the standard curve for known nicotinylalanine. The results are expressed as nanomoles of nicotinamide and nicotinylalanine per ml of plasma (nmol/ml).

The data shown in Table 1 demonstrate the effectiveness of nicotinylalanine and aspirin (ASA) for increasing plasma levels of nicotinamide and particularly over extended periods. The fact that chronic (2 Week) dosing of nicotinylalanine alone results in a return to nearly baseline levels of nicotinamide and a nearly ten-fold decrease in plasma nicotinylalanine levels (Table 1) is consistent with powerful regulatory mechanisms for nicotinamide involving its synthesis and degradation. However, this invention provides a means of maintaining elevated nicotinamide levels. Thus, the addition of ASA (aspirin) at 20 and 100 mg/kg increases the NAL-dependent nicotinamide plasma levels in a dose-related manner (while also increasing plasma levels of NAL and NAL-X). Maintenance of increased levels of nicotinamide and nicotinylalanine following administration of nicotinylalanine and a glycine conjugation inhibitor are consistent with an inhibition of a compensatory down regulation of nicotinamide.

TABLE 1

Nicotinamide (NAm), Nicotinylalanine (NAL), and an Unidentified Metabolite of Nicotinylalanine (NAL-X) Levels in Plasma of C57B1/6 Mice, Following Acute or Chronic (2 Weeks) Intraperitoneal Injections of 2R,2S-Nicotinylalanine (400 mg/Kg) Alone or In Combination with Acetyl-Salicylic Acid (ASA)

| Treatment Group (N) | Plasma Levels in nmoles/ml (Mean ± S.E.) | | |
|---|---|---|---|
| | NAm | NAL | NAL-X |
| PBS-Controls (8) (2 Weeks) | 4.3 ± 1.5[a] | N.D. | N.D. |
| Acute NAL (8) (Two Hours) | 7.4 ± 2.3 | 114.7 ± 65.6 | 57.3 ± 12.0 |
| Chronic NAL (8) (2 Weeks) | 4.7 ± 1.1 | 11.2 ± 4.5 | 14.9 ± 4.2 |
| Chronic NAL (8) & ASA (20 mg/kg) (2 Weeks) | 5.2 ± 0.6 | 1S.6 ± 4.1 | 16.0 ± 2.4 |
| Chronic NAL (8) & ASA (100 mg/kg) (2 Weeks) | 12.2 ± 2.3 | 90.3 ± 50.5 | 70.9 ± 17.0 |

C57BL/6 mice, 6 weeks of age were randomized to treatment groups and treated with NAL alone or in combination with ASA at the doses indicated for either a single dose (Acute) or for two weeks, Monday through Friday (Chronic). Mice were administered the drug in 0.02 ml/g body weight intraperitoneally and the pH of the solutions were adjusted to 6.8 to 7.4. Controls received PBS at the same volume dose on the same schedule. All mice were killed two hours after the 10th dose and blood was collected by cardiac puncture and stored on ice until centrifugation in a microfuge at 10,000 rpm to obtain plasma. Plasma was stored at −70° C. until analysis by the HPLC method of Stafford and Dennis (J. Chromatog. 582:145–151, 1992). Results are expressed as concentrations (nmol/mL of plasma) as determined by comparison to the standard curves. Spectral characteristics of an unidentified peak with retention time of approximately 16.7 minutes had similarity to that of authentic nicotinylalanine and because it was not observed in any other chromatographic runs from mice not injected with nicotinylalanine it was designated as an unknown metabolite of nicotinylalanine (NAL-X).
N.D. = Not detectable.

In summary, the data on the metabolic fates of nicotinamide and nicotinylalanine, following intraperitoneal injections of nicotinylalanine in combination with an inhibitor of glycine conjugation reactions, are consistent with enhanced cellular levels of nicotinamide at sites of functional importance. The complexity of these metabolic fates is apparent at the comparatively simple system of the inbred mouse maintained in a germ-free (micro-isolator cages) environment. Upon infection of these mice with a pathogen (e.g., LP-BM5 retrovirus), the metabolic system associated with nicotinamide becomes more complex due, in part, to hormones (cytokines) of the immune system. Thus, for example, interferon-gamma induces the rate-limiting enzyme (indoleamine 2,3-dioxygenase) in the kynurenine to nicotinamide pathway in all cells and tissues except for the liver where interferon-gamma inhibits the liver's rate-limiting enzyme (tryptophan pyrollase) in the kynurenine to nicotinamide pathway. An understanding and appreciation of this basic fact will facilitate interpretation of data from studies which will now be described on a mouse model of AIDS (murine acquired immune deficiency syndrome, MAIDS).

Example 2
Effect of Nicotinylalanine and Acetylsalicylic Acid Treatment of Mice in the Murine AIDS Model (MAIDS):

This study was designed to determine whether nicotinylalanine (NAL) alone or in combination with acetylsalicylic acid (ASA) will prevent or alter the course of murine retroviral-induced immunodeficiency disease, MAIDS, in C57BL/6 female mice. The LP-BM5 MuLV virus used for these studies was prepared from chronically infected SC-1 cells (ATCC Cat. No. CRL-1404), as described by Yetter R. A. et al., *J. Exp. Med.*, 168, 623–635, 1988. Mice were inoculated intraperitoneally (i.p.) with a known pool of this virus (Pool 66) such that 0.1 ml of the pool injected i.p. results in 100% of inoculated mice developing MAIDS. According to past experience with this pool of virus, 50% of vehicle-treated mice (virus positive controls) will die at approximately 18 to 20 weeks following inoculation. The MAIDS model is well characterized and reproducible in the laboratory, as described by Mosier D. E. et al., *J. Exp. Med.* 161, 766–784, 1985. By using a standard dose of the LP-BM5 virus to produce disease in 100% of mice and by using mice of the same sex and strain with no exposure to exogenous pathogens (and therefore little variability in immune competency), the MAIDS model could be successfully adapted for use as in in vivo screening of antiviral drugs and biological response modifiers having antiviral properties. Thus, for example, the MAIDS model has been used to define differential effectiveness of 3'azido-3'deoxythymidine (AZT) given in drinking water to mice over various time regimens-in relation to virus inoculation (Eiseman J. L. et al., *Antivir. Res.*, 16, 307–326, 1991).

Measures of disease progression followed the methods developed by Eiseman et al., 1991 (Ibid). Disease scores 0 through +4 are based upon body weight gain and palpable alterations in the size of lymph nodes and spleen. Severity of disease is scored as follows: 0.5, increased body weight and variably detected increase in size of any one lymph node or spleen; +1, clearly detectable increase in the size of a lymph node and spleen; +2, readily detectable (greater than 0.3 cm in diameter) increased size in more than one lymph node and, in particular, enlargement of subcervical, brachial or axillary nodes; +3, increased size of all palpable nodes and palpable splenomegaly ($\geq 0.3$ grams); +4, advanced disease with extensive splenomegaly (>1.0 grams) and lymphadenopathy.

Experimental procedures are outlined as follows:

Specific pathogen free, female C57BL/6 mice (5 weeks of age) were purchased from Charles River Breeding Laboratories. All mice were allowed one week to acclimate to housing facilities prior to randomization for study. Animals were marked for identification and placed in microisolator cages with identifying cards (5 mice/cage), where autoclaved food and water were provided ad libitum. In this efficacy study, the racemic mixture of NAL (Pharm-Eco Laboratories Inc., Lot SP239-113 AC), with or without ASA (Sigma Chemical Co., Lot 33H1104), was compared to AZT as a positive treatment in this assay system.

NAL and ASA were formulated under sterile conditions according to preformulation methods outlined in *Remington's Pharmaceutical Sciences Handbook*, 18th Edition, 1990, ibid). NAL and ASA were dissolved in sterile phosphate-buffered normal saline solution (i.e., vehicle; Biofluids Inc., Lot 413054), adjusted to between pH 7.2 to 7.4 with ION NaOH, sterilized by filtration through 0.2 $\mu$m bottle-type filters, and dispersed into sterile glass vials, sealed and capped (Wheaton Inc.). AZT (3'azido-3'deoxythymidine; Lot No. 809796) was a gift from Sandra Nusinoff-Lehman at Burroughs Wellcome Co. AZT was dissolved in sterile water to a concentration of 1.0 mg/ml and filtered through a 0.45 $\mu$m filter. The AZT-containing water was changed every Monday and Thursday and water consumption was recorded in order to calculate doses of AZT consumed throughout the study. The initial study had the following treatment groups (number of mice in each group):

Group 1, control MAIDS, i.p. vehicle (20)
Group 2, NAL, i.p. 200 mg/kg (20)
Group 3, NAL, i.p. 400 mg/kg (20)
Group 4, NAL, i.p. 400 mg/kg with ASA, i.p. 20 mg/kg (20)
Group 5, NAL, i.p. 400 mg/kg with AZT, drink (1 mg/ml) (20)
Group 6, NAL, i.p. 400 mg/kg begin two weeks post-virus (20)
Group 7, AZT drink (1 mg/ml) as positive controls (20)
Group 8, uninoculated control mice (10 mice).

Except for Group 6 (which began treatment 2 weeks after virus inoculation), test drug injections began 1 day after virus infection and continued every day except weekends (i.e., 5 times per week). However, for Groups 5 and 7, AZT was provided continuously in the drinking water. Therefor, in contrast to the test drugs, the AZT-treated mice had a sustained intake of a known, effective drug in this assay system.

Intermediate Evaluations:

Disease progression was monitored by measuring serum IgM levels by ELISA on all animals at monthly intervals during the course of disease. Three mice per group were randomly selected and sacrificed at monthly intervals (end of month one through four) of the study. Disease scores for each animal were recorded weekly based upon palpation of lymph nodes and spleen. Complete gross necropsies were performed on these euthanized animals and the ratio of recorded spleen to body weights was an additional indicator of diseases progression. Hematocrits were routinely assessed at monthly intervals on all animals in order to monitor hematopoietic toxicity of AZT and to evaluate potential hematopoietic toxicity associated with test drug treatments alone or in combination with ASA or with AZT. Infection was quantified by ecotropic virus XC plaque assays of spleens removed from the interim sacrificed animals. The study was to be terminated when mice were either dead or disease scores were +4 in more than 50% of the vehicle-treated MAIDS controls (Group 1), which occurred at 19 weeks post-inoculation of the virus pool. However, as the remaining mice in Group 1 were slow to progress towards more severe disease (FIG. 5) or death (FIG. 6), the study was extended until a termination date of 28 weeks post-inoculation. Thus, at 19 weeks post inoculation, it was predicted from disease scores attained by this juncture that greater than 90% of the mice in the NAL(400 mg/kg) combination doses and mice in the AZT alone (1 mg/mL) groups would survive beyond an additional 8 weeks of the original termination date.

Figure 5:
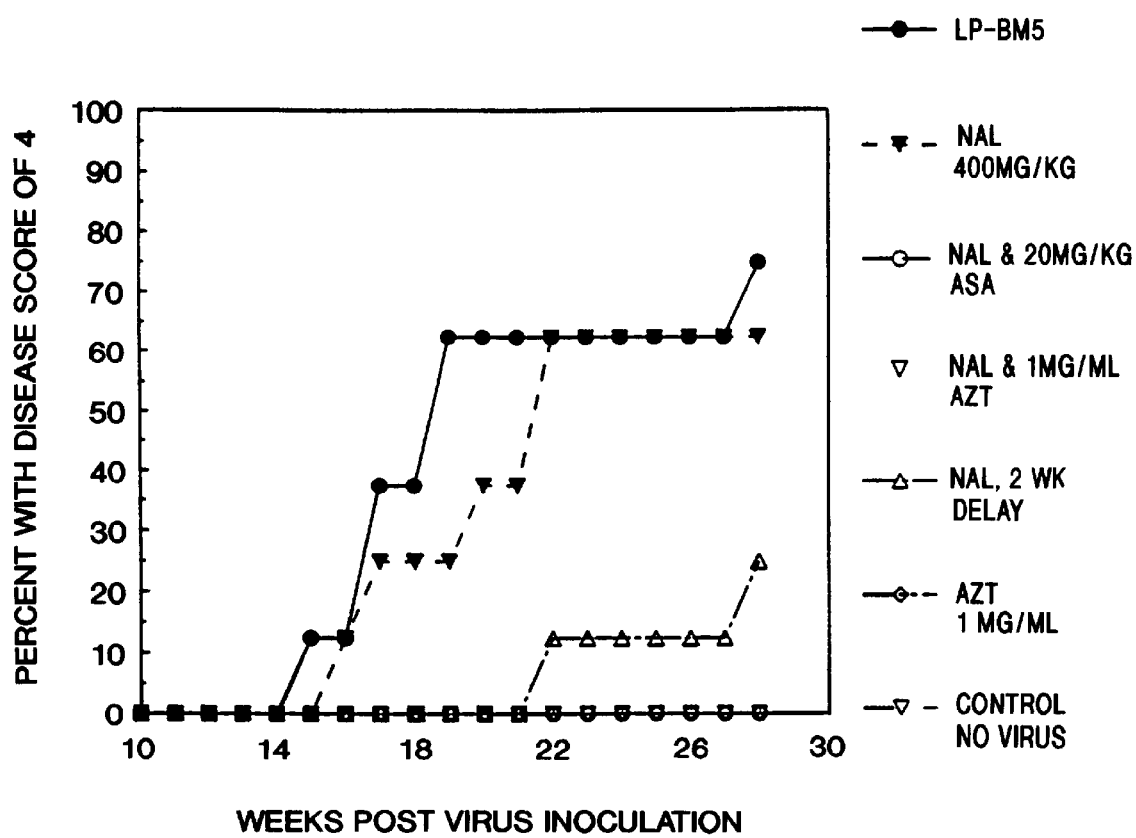
FIG. 5: Attainment of Disease Score of 4 in LP-BM5 Mice Treated with Nicotinylalanine (NAL) and/or Aspirin (ASA) and/or 3'-Azidothymidine (AZT), as Compared to Control Virus-Positive Mice Treated PBS-Vehicle Only. Each group consisted of 8 mice, except for the virus-negative control group which consisted of 6 mice. In this Kaplan-Meier plot of disease progression, there was no statistically significant difference between the control (solid circles) and NAL-Only (solid inverted triangles) groups. However, delaying the onset of NAL-Only treatment (400 mg/kg) to two weeks post-inoculation resulted in statistically significant suppression of disease progression as seen by the open triangles (Wilcoxon, Log-Rank statistical analysis, $p<0.05$). Combining NAL (400 mg/kg) with ASA (20 mg/kg) completely retarded disease progression to Stage 4 by 28 weeks after virus inoculation ($p=0.0052$), comparable to the efficacy shown by treatment with 1 mg/mL AZT in drinking water ($P=0.0027$).
Figure 6:
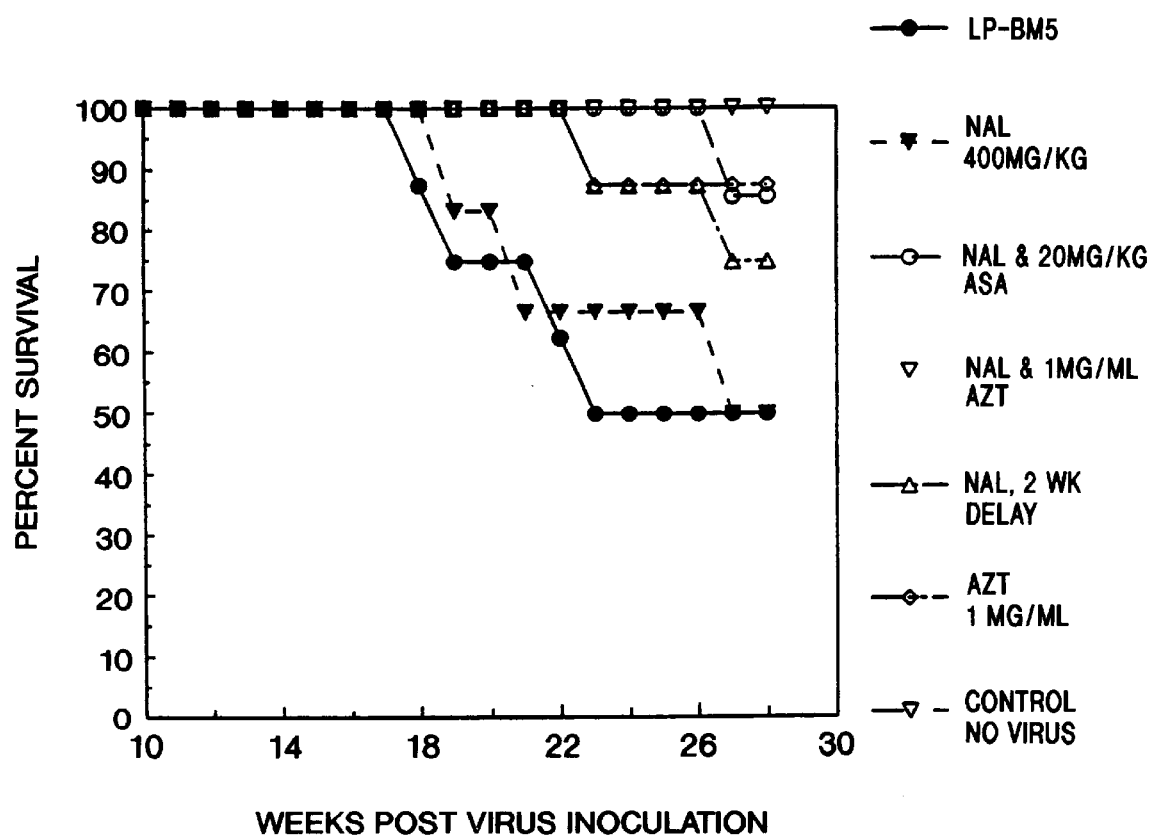
FIG. 6: Survival of LP-BM5 MuLV Retrovirus Infected Mice Treated with Nicotinylalanine (NAL) and/or Aspirin (ASA) and/or 3'-Azidothymidine (AZT), as Compared to Control Virus-Positive Mice Treated PBS-Vehicle Only. Each group consisted of 8 mice, except for the virus-negative control group which consisted of 6 mice. The data sets were analyzed using a Kaplan Meier estimation and Chi Squared test for overall significance which yielded a statistically significant p value of 0.0040 (significance was set at $p<0.05$). There was no statistically significant difference found between the control (solid circles) and NAL-Only (solid inverted triangles) group or the group receiving NAL after a two week delay (open triangles), $p=0.9621$ and $p=0.2492$, log-rank, respectively. However, the accelerated deaths among the LP-BM5 virus-positive control group (closed circles) was significantly different from all other groups, using log-rank transformations as follows: LP-BM5 versus NAL plus ASA, $p=0.0256$; LP-BM5 versus NAL plus AZT, $p=0.0256$; and LP-BM5 versus AZT Only, $p=0.0308$.

As shown in FIGS. 5 and 6, this prediction was experimentally verified by the fact that none of the 8 remaining mice in each of Groups 4, 5, or 7 progressed to disease scores greater than +2 (also deduced from the data in FIG. 1). However, one mouse in the AZT Alone (Group 7; Disease Score, 0.5) and two mice in the NAL plus ASA (Group 4; Disease Scores, 1 and 2) cohorts died prior to termination of the study. The two mice in the NAL plus ASA group appeared to have a prolonged period of weight loss prior to death and necropsy revealed hemorrhagic lungs in both mice. Pleural edema was also noted in one of these mice. The mouse in the AZT group had distended food filled small and large intestines and may have had intestinal blockage. These abnormalities could reflect opportunistic infection or some other disease process relatively independent of lymphadenopathy and immune suppression associated with LP-BM5 infection and MAIDS.

The Kaplan-Meier curves also indicate that the 400 mg/kg NAL therapy delayed by two weeks (Group 6) significantly retard disease progression as shown by a low percent of mice attaining a disease score of +4 (Log-Rank p=0.0469, Wilcoxon p=0.0258; FIG. 5). However, in terms of percent survival (FIG. 6), the delayed therapy with 400 mg/kg NAL alone did not significantly prolong survival as compared to the vehicle-injected control group (Log-Rank p=0.2492, Wilcoxon p=0.1756). Over the entire study, the rate of disease progression among mice in Group 6 appeared to be intermediate between the progression rates in Group 3 (NAL 400 mg/kg) and the AZT treatments (Groups 5 and 7) or the combination of NAL and aspirin (Group 4). Thus, as noted above, the combination of 400 mg/kg NAL and 20 mg/kg ASA significantly retards disease progression (FIG. 5) and enhances survival due to LP-BM5 retrovirus-induced MAIDS (FIG. 6). And, this combination treatment would be expected to have even greater efficacy if delayed two weeks, until the time of rapid B-cell proliferation.

Results from Monthly Interim Sacrifices:

As shown in Table 2-A, at 1 and 2 months, post virus inoculation, mice treated with NAL (400 mg/kg) in combination with ASA (20 mg/kg) had reduced disease progression of MAIDS, based on Disease Score and body weight as compared to vehicle-treated controls. The protective effect from AZT in the drinking water is more robust but hematopoietic toxicity was already manifest in the AZT-treated animals by one-month interim assessment (Table 3). In contrast to the combination therapy with ASA, treatment with racemic NAL alone (400 mg/kg) did not substantially retard progression of MAIDS (Tables 2-A & 2-B). Similarly, the 200 mg/kg doses of racemic NAL and the 400 mg/kg doses initiated two weeks after virus inoculation did not substantially retard disease progression (Tables 2-A & 2-B). However, the 400 mg/kg NAL treatments initiated two weeks post virus inoculation (Group 6) begin to show efficacy in the 3rd and 4th months against disease progression, as shown in Table 2-B and in FIG. 5. Moreover, interim results from Group 5 receiving 400 mg/kg doses of racemic NAL in combination with AZT (1 mg/ml in drinking water) were not substantially different than Group 7 which animals received AZT alone (Table 2-B).

In summary, in this evaluation of the efficacy of nicotinylalanine as a biologic response modifier, we have shown an early effect of racemic NAL (400 mg/kg) in combination with ASA (20 mg/kg) presented on a parenteral dosage schedule of five times per week. By retarding progression to MAIDS, this effect of a NAL-ASA combination (Group 4) appears to be intermediate between disease status in vehicle-treated controls (Group 1) and the continuous seven-day per week AZT-treated mice (Groups 5 and 7), as shown in Tables 2-A & 2-B. These results emphasize the importance of combination therapy with inhibitors of glycine conjugation (such as ASA) in order to effectively maintain NAL-dependent enhanced levels of nicotinamide as a functional inhibitor of poly(ADP)ribosylation reactions.

As indications of progression of disease in the MAIDS model, body and spleen weights and a clinical assessment yielding disease scores were used to follow treatment groups over time. Results for these items on three animals from each treatment group sacrificed monthly are tabulated in Table 2-A (one/two months) and Table 2-B (three/four months). In general a good correlation can be seen between these measures and the general conclusions from the progression data support the predictions from the Kaplan-Meier survival curves (see above).

TABLE 2-A

Some Disease-Related Outcomes from Interim Sacrifices at One and Two Months Postinoculation of LP-BM5 MuLV Retrovirus into C57BL/6 Mice.

| Experimental Group | Interim Data for 1-Month/2-Month | | | |
|---|---|---|---|---|
| | Mouse I.D. | Body Wt. (Grams) | Disease Score | Spleen Wt. (Grams) |
| Group 1: | 1/10 | 23.5/23.6 | 1/1 | 0.182/0.203 |
| V+ Vehicle-Injected | 13/15 | 22.6/21.9 | 1/1 | 0.239/0.142 |
| Controls | 19/17 | 24.8/23.1 | 1/2 | 0.180/0.233 |
| Group 2: | 23/21 | 21.9/22.5 | 0/1 | 0.080/0.229 |
| V+ NAL 200 mg/kg | 32/34 | 21.8/23.8 | 1/0.5 | 0.257/0.098 |
| (No ASA) | 40/37 | 23.4/22.2 | 0.5/2 | 0.123/0.302 |
| Group 3: | 45/51 | 21.3/21.6 | 1/1 | 0.186/0.289 |
| V+ NAL 400 mg/kg | 55/53 | 20.4/24.0 | 1/2 | 0.309/0.216 |
| (No ASA) | 59/56 | 19.6/24.0 | 1/1 | 0.159/0.125 |
| Group 4: | 68/65 | 18.6/22.9 | 1/0.5 | 0.266/0.129 |
| V+ NAL 400 mg/kg | 71/66 | 21.8/22.9 | 0.5/0 | 0.106/0.086 |
| & ASA 20 mg/kg | 77/79 | 20.9/20.6 | 0.5/1 | 0.085/0.200 |

TABLE 2-A-continued

Some Disease-Related Outcomes from Interim Sacrifices at One and Two Months Postinoculation of LP-BM5 MuLV Retrovirus into C57BL/6 Mice.

| | Interim Data for 1-Month/2-Month | | | |
|---|---|---|---|---|
| Experimental Group | Mouse I.D. | Body Wt. (Grams) | Disease Score | Spleen Wt. (Grams) |
| Group 5: | 83/81 | 19.2/21.8 | 0.5/0 | 0.097/0.108 |
| V⁺ NAL 400 mg/kg | 91/87 | 19.1/20.4 | 0/0 | 0.098/0.105 |
| & AZT 1 mg/ml | 99/95 | 20.8/20.9 | 0/0 | 0.095/0.125 |
| Group 6: | 104/105 | 20.4/21.2 | 0/1 | 0.103/0.168 |
| V⁺ NAL 400 mg/kg | 106/111 | 20.5/20.0 | 0.5/0 | 0.151/0.086 |
| Delayed Rx 2 Weeks | 120/119 | 22.3/26.6 | 0.5/2 | 0.136/0.320 |
| Group 7: | 124/126 | 21.1/20.9 | 0/0 | 0.097/0.090 |
| V⁺ AZT 1 mg/ml | 133/136 | 20.9/20.0 | 0.5/0 | 0.108/0.104 |
| in drink water | 137/140 | 19.6/22.6 | 0/0 | 0.096/0.086 |
| Group 8: | 147/148 | 20.6/21.3 | 0/0 | 0.069/0.087 |
| V⁻ Virus-negative, normal controls. | | | | |

Note: Three mice in each virus-positive (V⁺) experimental group were randomly selected for the 1-month and the 2-month interim sacrifice. Since the virus-negative group began with ten mice total, only one mouse was randomly selected for necropsy evaluation at the 1-month and 2-month times.

TABLE 2-B

Some Disease-Related Outcomes from Interim Sacrifices at Three and Four Months Postinoculation of LP-BM5 MuLV Retrovirus into C57BL/6 Mice.

| | Interim Data for 3-Month/4-Month | | | |
|---|---|---|---|---|
| Experimental Group | Mouse I.D. | Body Wt. (Grams) | Disease Score | Spleen Wt. (Grams) |
| Group 1: | 8/2 | 23.2/26.3 | 2/2 | 0.296/0.423 |
| V⁺ Vehicle-Injected | 11/4 | 23.0/28.3 | 0.5/3 | 0.096/0.648 |
| Controls | 18/20 | 23.2/29.2 | 2/4 | 0.254/1.125 |
| Group 3: | 41/42 | 23.6/27.6 | 0.5/0.5 | 0.112/0.119 |
| V⁺ NAL 400 mg/kg | 54/47 | 22.3/28.0 | 2/4 | 0.341/1.030 |
| (No ASA) | 60/57 | 24.6/25.5 | 0.5/2 | 0.086/0.240 |
| Group 4: | 61/63 | 26.3/27.5 | 2/1 | 0.310/0.219 |
| V⁺ NAL 400 mg/kg | 73/70 | 27.9/23.8 | 2/2 | 0.363/0.362 |
| & ASA 20 mg/kg | 80/78 | 25.4/27.1 | 2/3 | 0.261/0.317 |
| Group 5: | 85/84 | 23.0/24.1 | 0/0.5 | 0.074/0.115 |
| V⁺ NAL 400 mg/kg | 89/94 | 24.0/23.5 | 0.5/0.5 | 0.144/0.125 |
| & AZT 1 mg/ml | 92/100 | 24.5/25.3 | 0.5/0.5 | 0.124/0.109 |
| Group 6: | 103/107 | 23.8/26.8 | 0/3 | 0.090/0.399 |
| V⁺ NAL 400 mg/kg | 113/114 | 25.3/27.5 | 0.5/1 | 0.112/0.157 |
| Delayed Rx 2 Weeks | 118/117 | 26.3/24.5 | 1/0.5 | 0.175/0.083 |
| Group 7: | 123/125 | 23.8/25.0 | 0.5/2 | 0.118/0.262 |
| V⁺ AZT 1 mg/m | 128/131 | 23.5/21.1 | 0.5/0 | 0.114/0.086 |
| in drink water | 135/139 | 25.4/28.6 | 0.5/1 | 0.112/0.150 |

Note: Three mice in each virus-positive (V⁺) experimental group were randomly selected for the 3-month and the 4-month interim sacrifice. Since the virus-negative group began with ten mice total, only one mouse was randomly selected for necropsy evaluation at the 3-month and 4-month times. Data for Group 2 mice (V⁺ NAL 200 mg/kg) are not available as remaining mice entered a subprotocol after the second month, evaluating effects of combining vitamin B6 in the formulation.

Figure 4A:
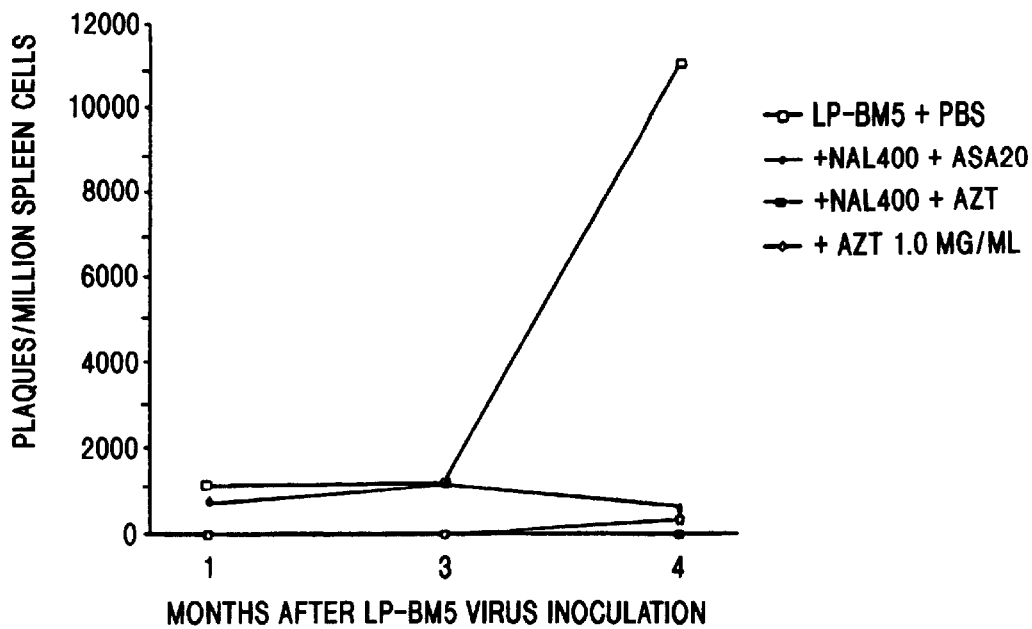
FIG. 4A and 4B: Mean Number of Virus Particles as Determined from Plaques per Million Spleen Cells from Serially Sacrificed Mice at Monthly Intervals After Inoculation with LP-BM5 Retrovirus. All mice as shown in these comparisons were injected intraperitoneally (i.p.) with Pool 66 of LP-BM5 murine leukemia virus on Day 1 of the study, with a known dilution of the virus pool which previously resulted in 100% of inoculated mice developing MAIDS. Each ml of the virus pool contained 3.66 log PFU ecotropic virus as determined by XC Plaque Assay. Treatment in all groups began one day after virus inoculation, except for the NAL 400 Delay Group which began treatment two weeks after virus inoculation. Groups and treatments are as follows.
Figure 4B:
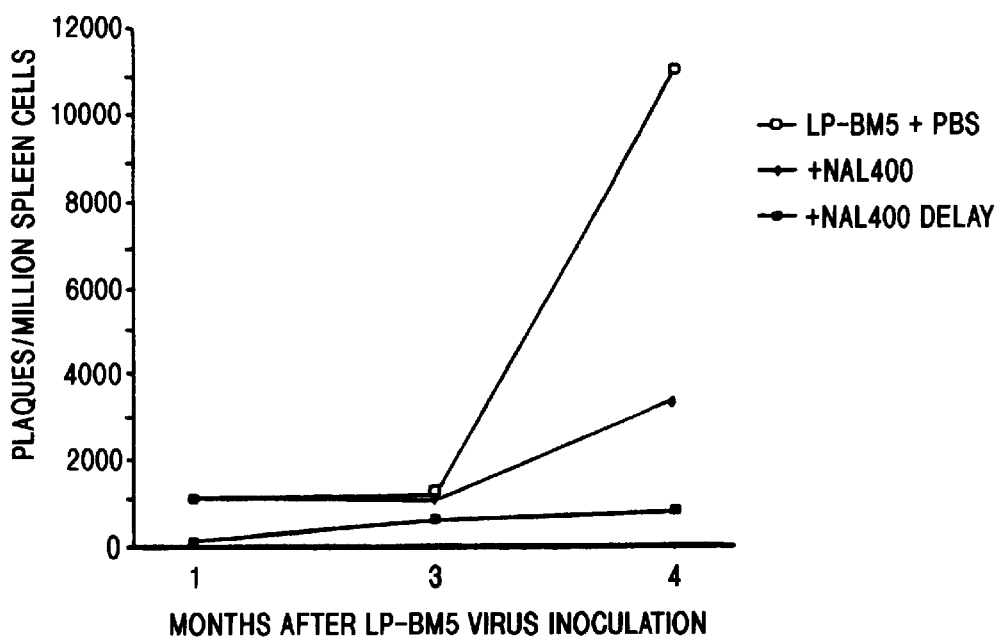

Ecotropic virus titers were determined using the XC plaque assay (Yetter R. A. et al., *J. Exp. Med.*, 168, 623–635, 1988) and were performed on spleen cells cultured from all serially killed mice at the interim sacrifices as shown in Tables 2-A & 2-B). Spleens were weighed and cells were extruded with sterile media (RPMI 1640, with gentamycin and 10% fetal calf serum). Serial 10-fold dilutions were made and one ml of each dilution was overlayered onto a monolayer of SC-1 cells treated with 4 μg/ml polybrene. After 24 hours, the media was removed and washed and the SC-1 cells were fed with fresh media. When the monolayer was confluent, the plates were irradiated with UV light at 60 ergs/mm²/sec and overlayered with XC cells. When the XC cell layer was confluent, the plates were fixed with methanol and stained with Giemsa Stain. Plaques were counted on an Artek colony counter and confirmed by phase contrast microscopy. Values presented in FIG. 4A represent the mean of adjusted samples at three dilutions expressed as plaques per million spleen cells. Mean and standard deviations corresponding to each of the data points in FIGS. 4A and 4B are derived from three mice serially killed at interim sacrifice times. Due to variability in the counts, statistical significance at the level of $p \leq 0.05$ was only found at four months following virus inoculation and for comparisons of the experimental groups (Groups 4–7) shown in FIGS. 4A and 4B with the vehicle-treated virus-positive control group (Group 1). Relevant mean values ± standard deviations for this quantitation of virus (expressed in plaques per million spleen cells) in each group are as follows: FIG. 4A: LP-BM5+PBS=11,043±9,437; NAL400+ASA20=650±347; NAL400+AZT (1 mg/mL)=0±0; and, AZT (1 mg/ML)= 333±495; FIG. 4B: LP-BM5+PBS=11,043±9,437; NAL400=3,410±4,606; and, NAL400 Delay=796±463.

In general, virus plaques appeared to correlate with spleen weights as shown in Tables 2-A and 2-B. Although AZT is able to block de novo infection, two of the mice treated with AZT for four months had detectable plaques indicating presence of replicating virus while none of three mice treated with AZT plus 400 mg/kg NAL had detectable virus in their spleens. In the other treatment protocols which used NAL at an i.p. dose of 400 mg/kg (M–F), with or without ASA or delayed for two weeks post-infection, virus was detectable in all interim sacrifices of mice but at a lower level as compared to the vehicle-injected LP-BM5-inoculated controls (FIGS. 4A,B).

Example 3

Effect of Nicotinylalanine and 3'Azido-3'deoxythymidine (AZT) Treatment in the Murine Aids Model of AIDS (MAIDS):

Dose response relationships of nicotinylalanine in combination with ASA were evaluated using the MAIDS model of mice infected with LP-BM5 virus. Intraperitoneal nicotinylalanine was evaluated at doses of 200 and 400 mg/kg. The 400 mg/kg nicotinylalanine dose was selected to be combined with ASA at a dose of 20 mg/kg body weight. This combination could also be used in conjunction with AZT treatment. Nicotinylalanine (400 mg/kg, i.p.) was combined with AZT (1 mg/kg in drinking water) for the purpose of comparison to AZT (1 mg/kg in drinking water) alone and to evaluate efficacy and toxicity in this comparison.

In regard to efficacy, nicotinylalanine (400 mg/kg) had no statistically significant effect (neither enhancing nor retarding) upon the antiviral or anti-disease properties of AZT in the mouse MAIDS model. However, chronic doses of AZT at 0.5 mg/kg in drinking water are also effective in controlling LP-BM5 disease and a lower dose of AZT at 0.1 mg/kg, while not as effective, still delayed disease progression (Eiseman J. L. et al., *Antiviral Res.*, 16:307–326, 1991).

Regarding toxicity, there are at least two documented side-effects of AZT in mice which were also observed to occur within the first month of dosing in the present study: (1) melaninization of extremities, tail, and ears; and, (2) red-blood cell toxicities. Neither of these AZT-associated toxicities was observed to be enhanced nor retarded by nicotinylalanine over the dosage (400 mg/kg) and course of this study. Quantitative data for red-blood cell toxicities are shown in Table 3. As shown in Table 3, normal (virus negative) control mice, housed in adjacent cages to the virus-infected groups, had rather consistent hematocrits of approximately 49% over 4 months of sampling. Both NAL plus AZT (Group 5) and AZT alone (Group 7) had rather consistent hematocrits over the four months sampled with mean values of approximately 41.1 and 42.6%, respectively. More variable and a tendency towards decreased hematocrit values, reaching a mean value of 43.3% at four months, were observed in the placebo-treated, virus positive control mice. This decreased hematocrit may reflect a pathologic outcome associated with some aspect of this chronic, progressive disease (e.g., vitamin or mineral deficiency). The observed protective effect of NAL plus ASA (Group 4) which was also observed in the NAL-delayed (Group 6) is another benefit of this invention which is more fully evaluated in Example 4.

TABLE 3

| | Mean Hematocrit in Percent (No. Bled Each Month) | | | |
|---|---|---|---|---|
| Exptl. Group | Month 1(10) | Month 2(10) | Month 3(7) | Month 4(11) |
| Group 1: $V^+$ PBS-Injected Controls | 46.6 + 4.8 | 48.1 + 1.9 | 47.4 + 2.3 | 43.3 + 7.8 |
| Group 3: $V^+$ NAL 400 mg/kg (No ASA) | 47.7 + 3.2 | 46.5 + 3.3 | 45.7 + 2.2 | 43.8 + 2.9 |
| Group 4: $V^+$ NAL 400 mg/kg ASA 20 mg/kg | 48.0 + 3.0 | 48.1 + 1.9 | 44.3 + 6.2 | 45.6 + 1.8 |
| Group 5: $V^+$ NAL 400 mg/kg AZT 1 mg/kg | 39.7 + 4.4 | 42.2 + 3.0 | 42.7 + 1.2 | 41.1 + 2.2 |
| Group 6: $V^+$ NAL 400 mg/kg Delayed Rx 2 weeks | 48.5 + 1.8 | 46.3 + 3.2 | 47.5 + 1.3 | 46.4 + 1.4 |
| Group 7: $V^+$ AZT 1 mg/kg | 41.7 + 4.0 | 42.7 + 2.4 | 41.9 + 1.7 | 42.6 + 3.0 |
| Group 8: $V^-$ Normal Controls | 49.5 + 1.7 | 49.3 + 1.8 | 48.5 + 1.4 | 48.4 + 0.8 |

Mice were maintained through the fifth month post virus inoculation until greater than 80% of vehicle-injected (PBS), virus-positive controls died. Any mice which died in the drug-treated groups (i.e., groups 2–7 in Table-3), died of recognizable LP-BM5 disease (e.g., enlarged spleens and lymph nodes) and not from obvious toxicities of the groups, singly or in combination.

Example 4

Plasma Nicotinamide Levels in Mice Infected with the LP-BM5 Virus and the Modulation of these Nicotinamide Levels by Nicotinylalanine Alone or in Combination with Aspirin or by AZT As shown in Table 4, by one-month after LP-BM5 retrovirus inoculation, placebo-treated control mice (Group 1) have mean circulating levels of nicotinamide approximately 35% lower than uninfected controls. The reason for this deficiency is not because of dietary insufficiency, since these mice ingested adequate amounts of vitamin-supplemented chow (Purina Autoclavable Rodent Chow) containing niacin and niacinamide (nicotinamide), but is due to the fact that circulating LP-BM5 virus in mice induces production of murine interferon-gamma (mIFN-γ) as a normal host response to viral infection. This cytokine induces indoleamine 2,3-dioxygenase (IDO) in a variety of cells and tissues and especially in cells of the monocyte lineage (macrophages, microglia, Kupfer cells, etc.). Reviewed in Taylor M. W. and Feng G., *FASEB J.* 5:2516–2522, 1991. In addition, IFN-γ down-regulates the enzyme tryptophan pyrollase in the liver (Takikawa O. et al., *J. Biol. Chem.* 263:2041–2048, 1988). Since it is the liver which utilizes dietary tryptophan for the de novo synthesis of nicotinamide for purposes of systemic distribution via the circulatory system, inhibition of tryptophan pyrollase effectively shuts down nicotinamide biosynthesis in the liver as the main source of circulating nicotinamide. Progressively decreased levels of plasma nicotinamide among the virus-positive control mice (Group 1, Table 4) are consistent with other evidence of increased circulating IFN-γ levels in mice and in humans up until terminal stages of disease from retroviral infection (Fuchs D. et al., *J. Interferon Res.* 10:599–603, 1990). On the contrary, treatment of infected mice (starting one day after inoculation) with chronic dosing of AZT in the drinking water effectively reduces circulating virus, resulting in plasma levels of nicotinamide which are similar to those found for virus-negative control mice (Table 4). Nicotinylalanine in combination with aspirin treatment according to this invention (Group 4, Table 4) also effectively prevents the precipitous fall in plasma nicotinamide levels observed in virus-positive controls. Although this latter effect of combination treatment could be due to some antiviral activity (see, e.g., FIG. 4A) and thereby reducing circulating IFN-γ levels, a more likely explanation would be related to the direct nicotinamide-enhancing metabolic effects of nicotinylalanine in combination with ASA. Nicotinamide-enhancing properties of all the experimental therapies which completed this study (i.e., Groups 3 through 7) were associated with effects by four months of the study as reflected by nearly 2:1 ratios between plasma levels in the experimental groups as compared to plasma levels in the placebo-treated control (Table 4).

TABLE 4

| | Mean Plasma Nicotinamide Levels (nMole/ml) | | | |
|---|---|---|---|---|
| Exptl. Group | Month 1 | Month 2 | Month 3 | Month 4 |
| Group 1: $V^+$ PBS-Injected Controls | 3.2 ± 0.5 | 3.9 ± 0.1 | 2.3 ± 0.5 | 2.5 ± 0.8 |
| Group 3: $V^+$ NAL 400 mg/kg (No ASA) | 3.4 ± 0.9 | 4.4 ± 0.5 | 3.1 ± 0.4 | 4.7 ± 0.5 |

TABLE 4-continued

| | | | | |
|---|---|---|---|---|
| Group 4:<br>V⁺ NAL 400 mg/kg<br>ASA 20 mg/kg | 4.0 ± 0.5 | 5.7 ± 0.6 | 3.5 ± 1.3 | 5.2 ± 1.1 |
| Group 5:<br>V⁺ NAL 400 mg/kg<br>AZT 1 mg/kg | 4.7 ± 1.8 | 7.4 ± 1.6 | 4.4 ± 0.7 | 5.8 ± 0.6 |
| Group 6:<br>V⁺ NAL 400 mg/kg<br>Delayed Rx 2 weeks | 3.7 ± 1.1 | 5.8 ± 0.5 | 3.8 ± 0.1 | 4.6 ± 0.3 |
| Group 7:<br>V⁺ AZT 1 mg/kg | 5.1 ± 0.6 | 6.0 ± 0.4 | 5.2 ± 3.0 | 5.8 ± 0.4 |
| Group 8:<br>V⁻ Normal Controls | 4.9 - | 6.3 - | 3.6 - | 4.6 - |

Comparisons of plasma nicotinamide mean values of treatment Groups to the placebo (PBS Control, Group 1), expressed as ratios are as follows:

| As Compared To Group 1 | RATIOS | | | |
|---|---|---|---|---|
| Group 3 (NAL Only): | 1.06 | 1.13 | 1.35 | 1.88 |
| Group 4 (NAL & ASA) | 1.25 | 1.46 | 1.52 | 2.08 |
| Group 5 (NAL & AZT) | 1.47 | 1.90 | 1.91 | 2.32 |
| Group 6 (NAL Delay) | 1.16 | 1.49 | 1.65 | 1.84 |
| Group 7 (AZT Only): | 1.59 | 1.54 | 2.26 | 2.32 |

Mice in this table correspond to interim sacrifice mice as shown in Tables 1 and 2. Mice were sacrificed on Tuesdays at monthly intervals after virus inoculation, approximately 24 hours after their last treatment. Three mice each comprise each of the virus-positive (V⁺) groups at the monthly intervals and one mouse each comprises the virus-negative (V⁻) normal control group at each monthly interval. Group 2 mice (200 mg/kg NAL) are not included in this table, as these mice were terminated after second month in study.
At time of sacrifice, blood was collected by cardiac puncture and stored on ice until centrifuged in a microfuge at 10,000 rpm to obtain plasma which was then stored frozen at −70° C. until analysis by the HPLC method of Stafford and Dennis (J. Chromatog. 582:145–151, 1992). Results are expressed as mean concentrations ± standard deviation in nanomoles/mL of plasma, as determined by comparison to the standard curve.

Example 5

Plasma Pharmacokinetics of Nicotinylalanine and Nicotinamide in Mice Following Intravenous, Intraperitoneal and Oral Administration of Nicotinylalanine The purpose of this study was to determine the plasma pharmacokinetics of nicotinylalanine in fasted, female C57BL/6 mice after intravenous (i.v.), intraperitoneal (i.p.), and oral (p.o.) administration of equivalent doses of nicotinylalanine at 400 mg/kg body weight. The analytic methods used in these studies were the same as described in Example 1 and Table 1 for Metabolic Studies.

Bioavailability of nicotinylalanine after p.o. and i.p. administration was determined by comparison of the areas under the plasma time curves with the area under the plasma time curve for the i.v. administration of an equivalent dose at 400 mg/kg into the tail vein. Time points were evaluated from five minutes to 1,440 minutes (24 hours) after dosing, although the rapid pharmacokinetics under each dosing regimen focused the time parameters to less than six hours.

Figure 7:
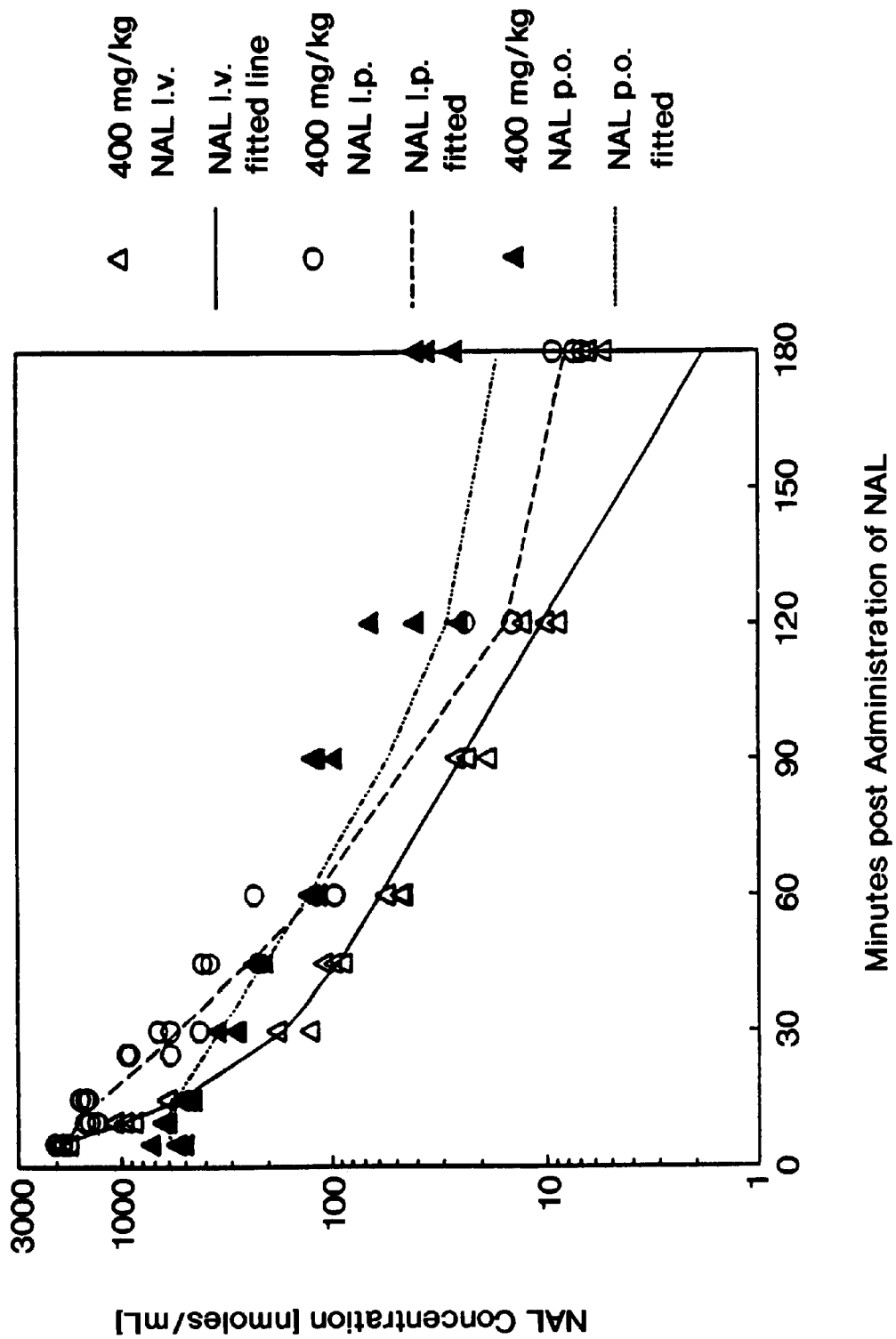
FIG. 7: Plasma concentration of nicotinylalanine (NAL) obtained after i.v., i.p., and p.o. administration of NAL at dosages of 400 mg/kg body weight. Data shown are replicate samples taken from three mice at each time point.
Figure 8:
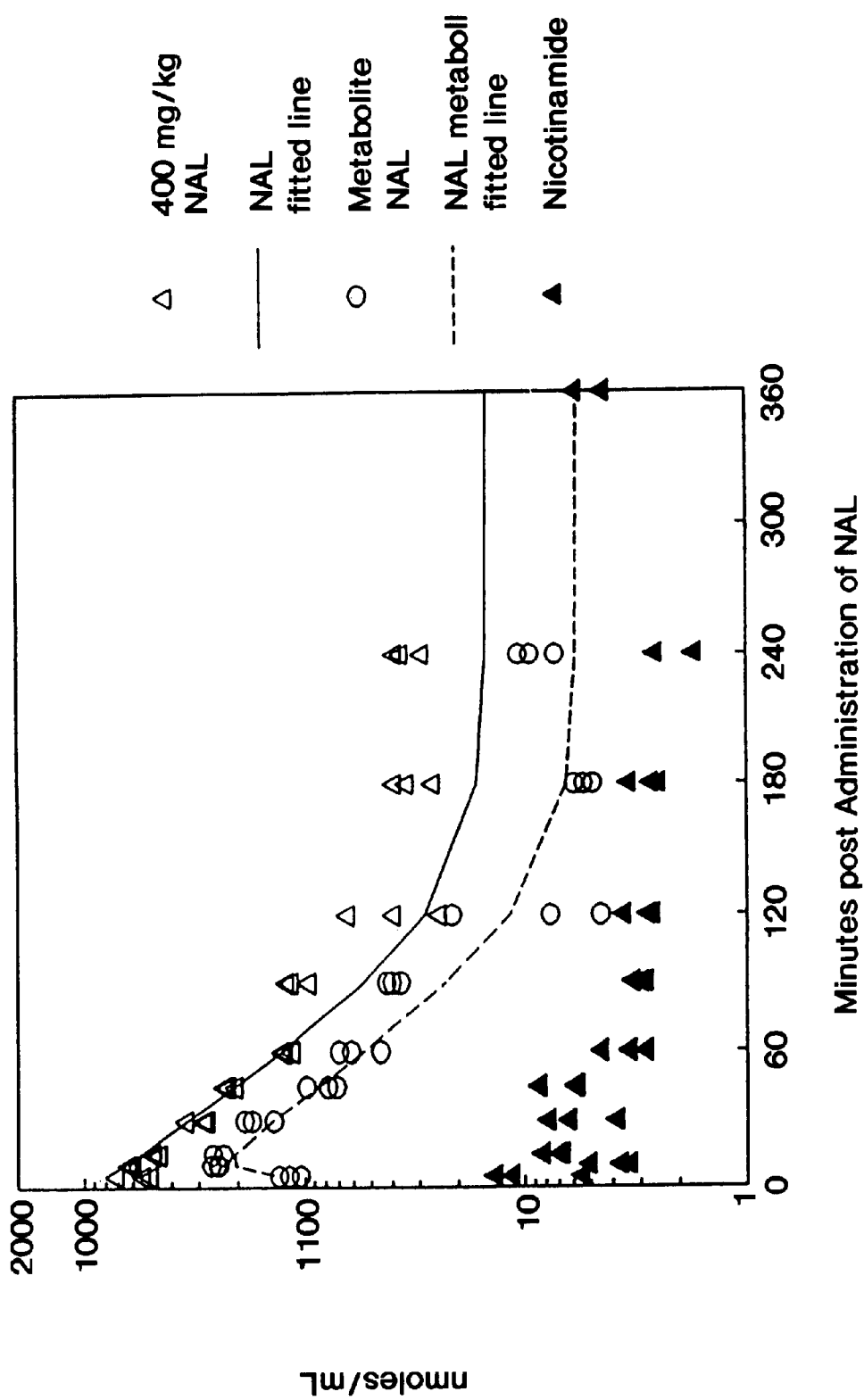
FIG. 8: Plasma concentrations of nicotinylalanine (NAL, open triangles), the nicotinylalanine metabolite (NAL-X, open circles) and nicotinamide (closed triangles), following a single oral dose of NAL at 400 mg/kg body weight. Data shown are replicate samples taken from three mice at each time point.

As shown in FIG. 7 peak plasma levels of nicotinylalanine (NAL) occur at approximately 5 minutes after either i.v. or i.p. administration of NAL at a dose of 400 mg/kg body weight, followed by a rapid decline. However, peak plasma levels of an equivalent oral dose (administered by oral gavage) were reached at approximately 10 minutes and these plasma levels were maintained for a prolonged time in contrast to the intravenous and intraperitoneal doses (FIGS. 7 and 8).

In Example 1, two hours after an acute, i.p., 400 mg/kg dose of NAL, plasma levels of NAL were about twice as high as plasma levels of a major NAL metabolite (designated NAL-X) and nicotinamide plasma levels were about twice those found in PBS-injected controls (Table 1). Similarly, following oral dosage of NAL the plasma ratio of parent compound NAL to NAL-X metabolite is about 2:1 from two hours to at least four hours after dosing (FIG. 8). Further, following an oral dose of NAL, transiently elevated levels of nicotinamide of about twice control (see Table 1) plasma levels were observed (FIG. 8).

Although there are several compartmental analyses which could be used to model the pharmacokinetic data, for derivation of pharmacokinetic parameters a simple non-compartmental analysis was selected. The computer program used to generate the parameters (Table 5) and for fitting the curves (FIGS. 7, 8) was the Lagran Program using the Lagrange Function. See, Rocci M. L. and Jusko W. J. 1983, "Lagran Program for Area and Moments in Pharmacokinetic Analysis", *Comp. Prog. Biomed.* 16, 203–212; and Yeh K. C. and Quan K. C. 1978, "A Comparison of Numerical Integrating Algorithms by Trapezoidal Lagrange and Spline Approximations", *J. Pharmacokinet. Biopharmacol.* 6, 79–93.

TABLE 5

Pharmacokinetic Parameters, Using Non-compartmental Analysis, Obtained for Nicotinylalanine (NAL), Following Administration of 2R,2S-Nicotinylalanine to Fasted Female C57BL/6 Mice

| | NAL Pharmacokinetic Parameters | | | | | |
|---|---|---|---|---|---|---|
| Dose. Route of NAL | AUC | Ke | t1/2 | Vdss | CL | F |
| 400 mg/kg, i.v. | 25865 | 0.0172 | 40.2 | 1332 | 57.3 | 1.0 |
| 400 mg/kg, i.p. | 47307 | 0.0278 | 24.9 | 821 | 31.6 | 1.83 |
| 400 mg/kg, p.o. | 27050 | 0.0118 | 58.7 | 3350 | 50.2 | 1.05 |

The kinetic data is relevant to optimizing dosage regimens of nicotinylalanine in combination with aspirin as a therapeutic agent. Thus, from the parameters summarized in Table 5, it is evident that the fraction bioavailable (F) after an oral dose is approximately 100% and equivalent to intravenous administration. Interestingly, the half-life (t½) of plasma nicotinylalanine following an oral dose (58.7 minutes) is approximately twice as long as after an i.p. dose and approximately one and a half (1½) times as long as after i.v. administration (Table 5). Further, the volume of distribution (Vdss) is consistent with a compound well-distributed in aqueous compartments, especially in the oral dosage form.

Based on the data presented in Table 5, an optimum protocol would include both oral and i.p. administration since both the duration of action (t½) and bioavailability (F) would be maximized.

While we have hereinbefore described a number of embodiments of this invention, it is apparent that the basic constructions can be altered to provide other embodiments which utilize the methods and compositions of the invention. Therefore, it will be appreciated that the scope of this invention is defined by the claims appended hereto rather than by the specific embodiments which have presented hereinbefore by way of example.

I claim:
1. A composition comprising a compound of formula II

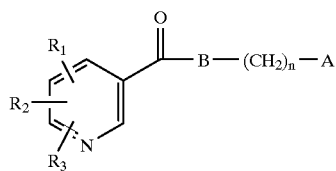

(II)

wherein $R_1$, $R_2$, and $R_3$ are independently, the same or different and may be selected from the group consisting of hydrogen, halogen, amino, nitro, hydroxyl, ethoxycarbonyl, carboxyl, carbamoyl, carbamoyloxy, and an optionally substituted $C_{1-2}$ alkyl wherein the alkyl group may be substituted with a halogen, amino, nitro, or hydroxyl group;
B is either a bond, NH or oxygen;
A is selected from the group consisting of $CR_4NH_2COOH$, $CR_5R_6R_7$, and $NR_5R_6$, and
wherein $R_4$ is selected from hydrogen; amino; hydroxyl; ethoxycarbonyl; carbamoyl; an optionally substituted $C_{1-2}$ alkyl wherein the alkyl group may be substituted with a halogen, amino, nitro, or hydroxyl group; a side chain of a naturally occurring amino acid optionally substituted at the α carbon with H or any of a series of heterocyclic groupings, including pyridinyl, imidazolyl, phenyl, or indolyl;
and wherein $R_5$, $R_6$ and $R_7$ are the same or different and are selected from the group consisting of $C_{1-4}$ alkyl, hydrogen, and phenyl, pyridinyl, imidazolyl or indolyl; $COOCH_2R_8$
wherein $R_8$ is selected from the group consisting of phenyl, pyridinyl, imidazolyl, and indolyl, and wherein n is 0, 1, 2 or 3;
and at least one compound selected from the group consisting of vitamin B6 and inhibitors of glycine conjugation associated with the metabolism of nicotinamide.
2. The composition according to claim 1 wherein the compound of formula II is nicotinylalanine, and comprising an inhibitor of glycine conjugation selected from the group consisting of aspirin, sodium benzoate, sodium phenylacetate, sodium 1-napthylacetate, sodium isovalerate, and bromosulfophthalein.
3. The composition according to claim 2 wherein the inhibitor of glycine conjugation is aspirin.
4. The composition according to claim 3 wherein the nicotinylalanine and aspirin together are present in the composition in an amount sufficient to increase plasma concentrations of nicotinamide above control levels in an individual administered said composition.
5. The composition according to claim 3 wherein nicotinylalanine is present in the composition at between about 0.5 and about 5.0 gm and aspirin is present in the composition at between about 0.2 and about 2.0 gm.
6. The composition according to claim 5 wherein nicotinylalanine is present in the composition at between about 1.0 and about 4.0 gm and aspirin is present in the composition at between about 0.5 and about 1.5 gm.
7. The composition according to claim 6 wherein nicotinylalanine is present in the composition at between about 1.0 and about 3.0 gm and aspirin is present in the composition at between about 0.5 and about 1.5 gm.
8. The composition according to claim 7 wherein nicotinylalanine is present in the composition at between about 1.0 and about 2.0 gm and aspirin is present in the composition at between about 0.5 and 1.0 gm.
9. The composition according to claim 1 wherein the compound of formula II is nicotinylalanine and further comprising vitamin B6.
10. A. The composition according to claim 9 wherein nicotinylalanine is present in the composition at between about 0.5 and about 5.0 gm and vitamin B6 is present in the composition at between about 2 and 300 mg.
11. The composition according to claim 10 wherein nicotinylalanine is present in the composition at between about 1.0 and about 4.0 gm and vitamin B6 is present in the composition at between about 5 and about 150 mg.
12. The composition according to claim 11 wherein nicotinylalanine is present in the composition at between about 1.0 and about 3.0 gm and vitamin B6 is present in the composition at between about 10 and about 100 mg.
13. The composition according to claim 12 wherein nicotinylalanine is present in the composition at between about 1.0 and about 3.0 gm and vitamin B6 is present in the composition in an amount sufficient to achieve a dose of about 0.2 to about 1.0 mg/kg body weight in an individual administered said composition.
14. The composition according to claim 1 comprising nicotinylalanine, aspirin and vitamin B6.
15. The composition according to claim 14 wherein nicotinylalanine is present in the composition at between about 0.5 and about 5.0 gm, aspirin is present in the composition at between about 0.2 and about 2.0 gm and vitamin B6 is present in the composition in an amount sufficient to achieve a dose of about 0.2 to about 1.0 mg/kg.
16. The composition according to claim 15 wherein nicotinylalanine is present in the composition at between about 1.0 and about 4.0 gm and aspirin is present in the composition at between about 0.5 and about 1.5 gm.
17. The composition according to claim 16 wherein nicotinylalanine is present in the composition at between about 1.0 and about 3.0 gm and aspirin is present in the composition at between about 0.5 and about 1.5 gm.
18. The composition according to claim 17 wherein nicotinylalanine is present in the composition at between about 1.0 and about 2.0 gm and aspirin is present in the composition at between about 0.5 and 1.0 gm.
19. A method of reducing cellular toxicity associated with poly-(ADP)-ribosylation comprising providing to cells a composition comprising a compound of formula II

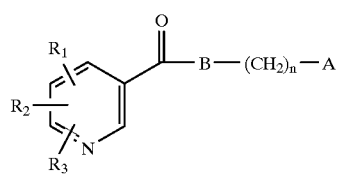

(II)

wherein $R_1$, $R_2$, and $R_3$ are independently, the same or different and may be selected from the group consisting of hydrogen, halogen, amino, nitro, hydroxyl, ethoxycarbonyl, carboxyl, carbamoyl, carbamoyloxy, and an optionally substituted $C_{1-2}$ alkyl wherein the alkyl group may be substituted with a halogen, amino, nitro, or hydroxyl group;
B is either a bond, NH or oxygen;
A is selected from the group consisting of $CR_4NH_2COOH$, $CR_5R_6R_7$, and $NR_5R_6$, and
wherein $R_4$ is selected from hydrogen; halogen; amino; nitro; hydroxyl; ethoxycarbonyl; carboxyl; carbamoyl;

carbamoyloxy; an optionally substituted $C_{1-2}$ alkyl wherein the alkyl group may be substituted with a halogen, amino, nitro, or hydroxyl group; a side chain of a naturally occurring amino acid optionally substituted at the a carbon with H or any of a series of heterocyclic groupings, including pyridinyl, imidazolyl, phenyl, or indolyl;

and wherein $R_5$, $R_6$ and $R_7$ are the same or different and are selected from the group consisting of $C_{1-4}$alkyl, hydrogen, and phenyl, pyridinyl, imidazolyl or indolyl; $COOCH_2R_8$ wherein $R_8$ is selected from the group consisting of phenyl, pyridinyl, imidazolyl, and indolyl, and wherein n is 0, 1, 2 or 3; and at least one compound selected from the group consisting of vitamin B6 and inhibitors of glycine conjugation associated with the metabolism of nicotinamide, and wherein the composition is provided in amount sufficient to increase the concentration of cellular nicotinamide.

20. The method according to claim 19 wherein the compound of formula II is nicotinylalanine and the inhibitor of glycine conjugation is selected from the group consisting of aspirin, sodium benzoate, sodium phenylacetate, sodium 1-napthylacetate, sodium isovalerate, and bromosulfophthalein.

21. The method according to claim 20 wherein the inhibitor of glycine conjugation is aspirin.

22. The method according to claim 21 wherein the nicotinylalanine and the aspirin are provided to the cells so as to expose the cells to a solution comprising about 200 to about 1000 nmole/ml nicotinylalanine and about 100 to about 200 nmole/ml aspirin.

23. The method according to claim 19 wherein the compound of formula II is nicotinylalanine and wherein the composition further comprises vitamin B6.

24. The method according to claim 23 wherein the nicotinylalanine is provided to the cells so as to expose the cells to a solution comprising about 200 to about 1000 nmole/ml nicotinylalanine.

25. The method according to claim 19 wherein the composition comprises nicotinylalanine, aspirin and vitamin B6.

26. The method according to claim 25 wherein the nicotinylalanine and the aspirin are provided to the cells so as to expose the cells to a solution comprising about 200 to about 1000 nmole/ml nicotinylalanine and about 100 to about 200 nmole/ml aspirin.

27. A pharmaceutical composition comprising a compound of formula II

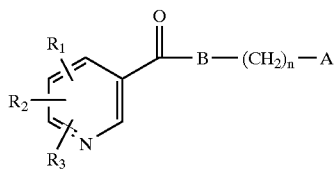

(II)

wherein $R_1$, $R_2$, and $R_3$ are independently, the same or different and may be selected from the group consisting of hydrogen, halogen, amino, nitro, hydroxyl, ethoxycarbonyl, carboxyl, carbamoyl, carbamoyloxy, and an optionally substituted $C_{1-2}$ alkyl wherein the alkyl group may be substituted with a halogen, amino, nitro, or hydroxyl group;

B is either a bond, NH or oxygen;

A is selected from the group consisting of $CR_4NH_2COOH$, $CR_5R_6R_7$, and $NR_5R_6$, and wherein $R_4$ is selected from hydrogen; halogen; amino; nitro; hydroxyl; ethoxycarbonyl; carboxyl; carbamoyl; carbamoyloxy; an optionally substituted $C_{1-2}$ alkyl wherein the alkyl group may be substituted with a halogen, amino, nitro, or hydroxyl group; a side chain of a naturally occurring amino acid optionally substituted at the a carbon with H or any of a series of heterocyclic groupings, including pyridinyl, imidazolyl, phenyl, or indolyl;

and wherein $R_5$, $R_6$ and $R_7$ are the same or different and are selected from the group consisting of $C_{1-4}$ alkyl, hydrogen, and phenyl, pyridinyl, imidazolyl or indolyl; $COOCH_2R_8$ wherein $R_8$ is selected from the group consisting of phenyl, pyridinyl, imidazolyl, and indolyl, and wherein n is 0, 1, 2 or 3; and at least one compound selected from the group consisting of vitamin B6 and inhibitors of glycine conjugation associated with the metabolism of nicotinamide, wherein the composition is effective for increasing the concentration of endogenous nicotinamide in an individual administered said composition.

28. The pharmaceutical composition according to claim 27 wherein the compound of formula II is nicotinylalanine and wherein the inhibitor of glycine conjugation is selected from the group consisting of aspirin, sodium benzoate, sodium phenylacetate, sodium 1-napthylacetate, sodium isovalerate, and bromosulfophthalein.

29. The pharmaceutical composition according to claim 28 wherein the inhibitor of glycine conjugation is aspirin.

30. The pharmaceutical composition according to claim 29 wherein the nicotinylalanine is present in the composition in an amount sufficient to increase endogenous concentrations of nicotinamide and wherein aspirin is present in the composition in an amount sufficient to reduce the metabolism of endogenous nicotinamide.

31. The pharmaceutical composition according to claim 29 wherein nicotinylalanine is present in the composition at between about 0.5 and about 5.0 gm and aspirin is present in the composition at between about 0.2 and about 2.0 gm.

32. The pharmaceutical composition according to claim 31 wherein nicotinylalanine is present in the composition at between about 1.0 and about 4.0 gm and aspirin is present in the composition at between about 0.5 and about 1.5 gm.

33. The pharmaceutical composition according to claim 32 wherein nicotinylalanine is present in the composition at between about 1.0 and about 3.0 gm and aspirin is present in the composition at between about 0.5 and about 1.5 gm.

34. The pharmaceutical composition according to claim 33 wherein nicotinylalanine is present in the composition at between about 1.0 and about 2.0 gm and aspirin is present in the composition at between about 0.5 and 1.0 gm.

35. The pharmaceutical composition according to claim 33 further comprising vitamin B6.

36. The pharmaceutical composition according to claim 35 wherein the vitamin B6 is present in the composition in an amount sufficient to achieve a dose of about 0.2 to about 1.0 mg/kg.

37. A method of increasing cellular nicotinamide levels in an individual, the method comprising administering to said individual a pharmaceutical composition according to claim 27.

38. The method according to claim 37 wherein compound of formula II is nicotinylalanine and the inhibitor of glycine conjugation is selected from the group consisting of aspirin, sodium benzoate, sodium phenylacetate, sodium 1-napthylacetate, sodium isovalerate, and bromosulfophthalein.

39. The method according to claim 38 wherein the inhibitor of glycine conjugation is aspirin.

40. The method according to claim 39 wherein the nicotinylalanine is present in the composition in an amount sufficient to increase endogenous concentrations of nicotinamide and wherein aspirin is present in the composition in an amount sufficient to reduce the metabolism of endogenous nicotinamide.

41. The method according to claim 39 wherein nicotinylalanine is present in the composition at between about 0.5 and about 5.0 gm and aspirin is present in the composition at between about 0.2 and about 2.0 gm.

42. The method according to claim 41 wherein nicotinylalanine is present in the composition at between about 1.0 and about 4.0 gm and aspirin is present in the composition at between about 0.5 and 1.5 gm.

43. The method according to claim 42 wherein nicotinylalanine is present in the composition at between about 1.0 and about 3.0 gm and aspirin is present in the composition at between about 0.5 and 1.5 gm.

44. The method according to claim 43 wherein nicotinylalanine is present in the composition at between about 1.0 and about 2.0 gm and aspirin is present in the composition at between about 0.5 and 1.0 gm.

45. The method according to claim 37 wherein the amounts of nicotinylalanine and aspirin in the composition are sufficient to produce in said individual a plasma level of nicotinylalanine between about 200 to about 1000 nmole/ml and a plasma level of aspirin between about 100 and about 200 nmole/ml.

46. The method according to claim 45 wherein the composition administered to the individual further comprises vitamin B6.

47. A method of treatment of an individual having a disease characterized by a pathogenic process involving activation of poly (ADP-ribose) synthetase, comprising raising the cellular nicotinamide level in said individual by administering to said individual a pharmaceutical composition according to claim 27.

48. The method according to claim 37 wherein the composition is administered in an amount sufficient to achieve plasma nicotinamide concentrations of between about 0.5 and about 20 nmole/ml.

49. The method according to claim 47 wherein the disease being treated is further characterized by cellular damage resulting from nitric oxide.

50. The method according to claim 47 wherein the disease being treated is a disease selected from the group consisting of neurodegenerative, viral, neoplastic and autoimmune diseases.

51. The method according to claim 50 wherein the disease being treated is a viral disease caused by HIV-1.

52. The method according to claim 47 wherein the disease being treated is selected from the group consisting of AIDS, epilepsy, neurotoxicity associated with vascular stroke, Huntington's Disease, Alzheimer's Disease, Schizophrenia, Parkinson's Disease, cancer and diabetes type 1.

53. The method according to claim 47 wherein the pharmaceutical composition comprises nicotinylalanine and aspirin.

54. The method according to claim 53 wherein nicotinylalanine is present in the composition at between about 0.5 and about 5.0 gm and aspirin is present in the composition at between about 0.2 and about 2.0 gm.

55. The method according to claim 54 wherein nicotinylalanine is present in the composition at between about 1.0 and about 4.0 gm and aspirin is present in the composition at between about 0.5 and about 1.5 gm.

56. The method according to claim 55 wherein nicotinylalanine is present in the composition at between about 1.0 and about 3.0 gm and aspirin is present in the composition at between about 0.5 and about 1.5 gm.

57. The method according to claim 56 wherein nicotinylalanine is present in the composition at between about 1.0 and about 2.0 gm and aspirin is present in the composition at between about 0.5 and 1.0 gm.

58. The method according to claim 54 wherein the disease being treated is AIDS.

59. The method according to claim 54 wherein the disease being treated is diabetes mellitus type 1.

60. The method according to claim 54 wherein the disease is a neurodegenerative disease.

61. The method according to claim 60 wherein the neurodegenerative disease is selected from the group consisting of epilepsy, neurotoxicity associated with vascular stroke, Huntington's Disease, Alzheimer's Disease, Schizophrenia, and Parkinson's Disease.

62. The method according to claim 61 wherein the disease is cancer.

63. The method according to any one of claims 58–62 wherein the amounts of nicotinylalanine and aspirin in the composition are sufficient to produce in said individual a plasma level of nicotinylalanine between about 200 to about 1000 nmole/ml and a plasma level of aspirin between about 100 and about 200 nmole/ml.

64. The method according to claim 63 wherein the composition further comprises vitamin B6.

65. The method according to claim 63 wherein the composition is administered to an individual in an amount sufficient to achieve plasma nicotinamide concentrations of between about 0.5 and about 20 nmole/ml.

66. The method according to claim 65 wherein the composition is administered to an individual in an amount sufficient to achieve plasma nicotinamide concentrations of between about 1.0 and about 10.0 nmole/ml.

67. The method according to claim 66 wherein the composition is administered to an individual in an amount sufficient to achieve plasma nicotinamide concentrations of between about 2.0 and about 5.0 nmole/ml.

* * * * *

UNITED STATES PATENT AND TRADEMARK OFFICE
CERTIFICATE OF CORRECTION

PATENT NO : 5,916,906
DATED : June 29, 1999
INVENTOR(S) : Edward G. Shaskan

It is certified that error appears in the above-identified patent and that said Letters Patent is hereby corrected as shown below:

Column 20, line 45, "1S.6" should read – – 15.6 – – . Column 29, line 40, "Nicotinvlalanine" should read – – Nicotinylalanine – –. Column 32, line 6, after "10." delete "A.". Column 33, line 5 and column 34, line 6, for "the a carbon", each occurrence should read – – the α carbon – –. Column 36, line 32, "claim 61" should read – – claim 54 – –.

Signed and Sealed this

Eighth Day of February, 2000

Attest:

Q. TODD DICKINSON

Attesting Officer

Commissioner of Patents and Trademarks